(12) United States Patent
Silverman

(10) Patent No.: US 6,221,056 B1
(45) Date of Patent: Apr. 24, 2001

(54) STRONG DIAPHRAGM/SAFE NEEDLE UNITS AND COMPONENTS FOR TRANSFER OF FLUIDS

(76) Inventor: David G. Silverman, 3 Meeker Hill Rd., Redding, CT (US) 06896

( * ) Notice: Subject to any disclaimer, the term of this patent is extended or adjusted under 35 U.S.C. 154(b) by 0 days.

(21) Appl. No.: 08/994,959

(22) Filed: Dec. 19, 1997

Related U.S. Application Data

(60) Provisional application No. 60/033,720, filed on Dec. 20, 1996.

(51) Int. Cl.[7] ............................................. A61M 5/00
(52) U.S. Cl. ..................... 604/239; 604/272; 604/167.02
(58) Field of Search ........................ 604/181, 117, 604/170, 239, 256, 272, 274, 275, 905, 93.01, 167.01, 167.02, 167.04

(56) References Cited

U.S. PATENT DOCUMENTS

| | | | |
|---|---|---|---|
| 3,931,010 | * | 1/1976 | Ayres et al. ............................ 210/109 |
| 5,199,948 | * | 4/1993 | McPhee .................................. 604/86 |
| 5,211,650 | * | 5/1993 | Noda .................................... 606/139 |
| 5,478,328 | * | 12/1995 | Silverman et al. ................... 604/272 |
| 5,759,178 | * | 6/1998 | Wells .................................... 604/240 |
| 5,788,679 | * | 8/1998 | Gravlee, Jr. ........................... 604/272 |
| 5,848,996 | * | 12/1998 | Eldor .................................... 604/272 |
| 5,858,001 | * | 1/1999 | Tsals et al. ............................ 604/135 |

* cited by examiner

Primary Examiner—Anhtuan T. Nguyen
Assistant Examiner—Jeremy Thissell
(74) Attorney, Agent, or Firm—Ostrolenk, Faber, Gerb & Soffen, LLP

(57) ABSTRACT

A needle has a blunted tip and a recessed orifice to avoid unintentional needle sticks and user contact with inoculum contained in the needle. A diaphragm is designed for use with the relatively blunt tip needle so that the needle easily penetrates the diaphragm at a force substantially lower than the force required to puncture skin, preferably at most 50% of the force required to puncture skin.

29 Claims, 27 Drawing Sheets

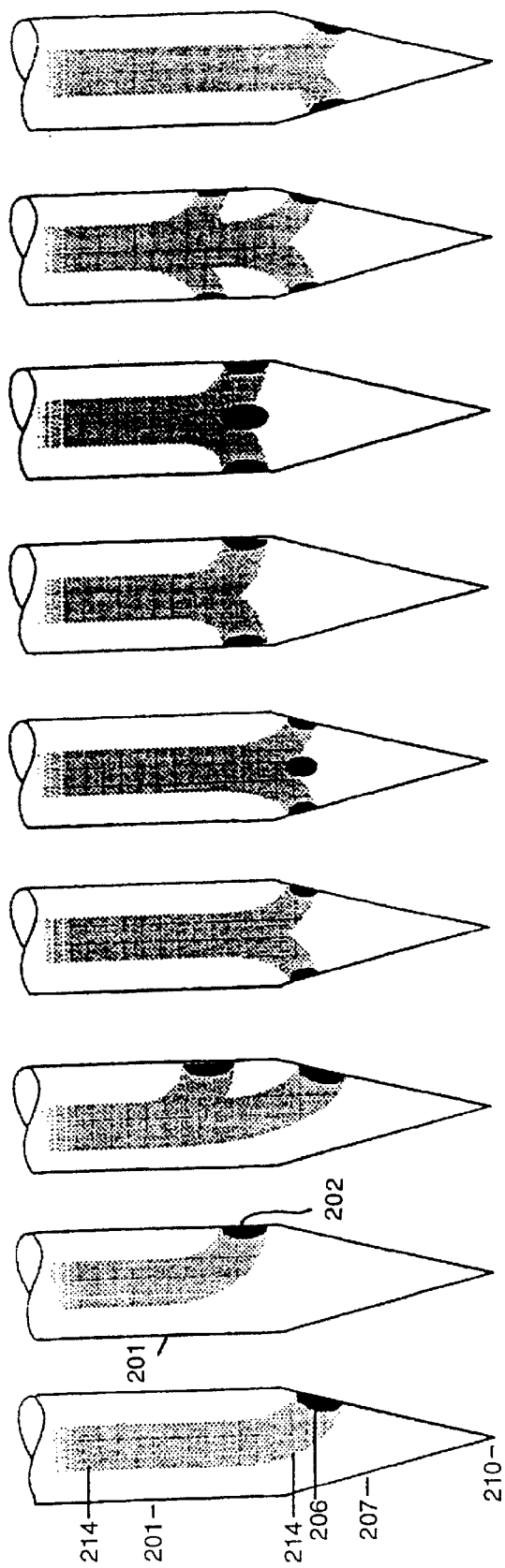

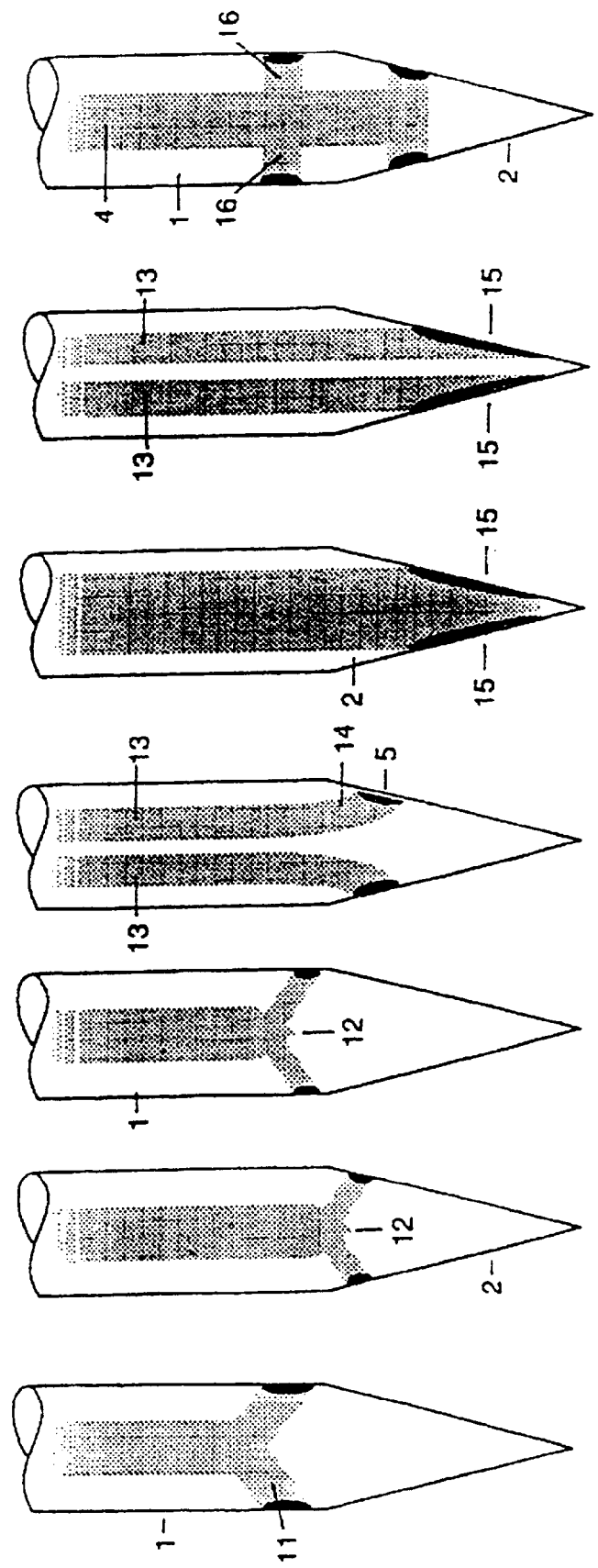

STRONG DIAPHRAGM/SAFE NEEDLE UNITS AND COMPONENTS FOR TRANSFER OF FLUIDS

CROSS-REFERENCE TO RELATED APPLICATIONS

This application is based on U.S. provisional application No. 60/033,720 filed Dec. 20, 1996, incorporated by reference.

It is related to the applicant's prior U.S. Pat. 5,478,328 issued Dec. 26, 1995, incorporated by reference.

It is noted that the applicant has filed on even date herewith, a three-part series of disclosures, incorporated by reference as follows I =The present application "Strong Diaphragm/Safe Needle Units and Components for Transfer of Fluids", Ser. No. 09/994,959;

II ="Strong Diaphragm/Safe Needle/Converting Device Combinations and Their Individual Components", Ser. No. 08/994,718; and III ="Reversibly Compressed Prechannelled/ Preweakened Diaphragms for Use with Blunt Cannulae and Safe Needles", Ser. No. 08/994,087.

BACKGROUND OF THE INVENTION

The present series of inventions was prompted by the obvious need to decrease the exposure of healthcare workers to potentially harmful needle sticks which, as detailed in the inventors' recent disclosure (U.S. Pat. No. 5,478,328 in 1995), pose the risk of infection with diseases such as hepatitis and AIDS. All too commonly, inadvertent needle sticks occur with needles that are being used for, or have been used for, penetrating a diaphragm. The varied uses of such needle/diaphragm combinations include: (a) withdrawing from or injecting into a medication vial, collection tube, or fluid bag; (b) injecting or withdrawing medications or fluids via tubing attached to an intravenous catheter.

The common features of the present series of inventions include needle/diaphragm combinations wherein:

(a) "safe yet penetrating" needles, such as those illustrated, in part, in our prior patent (U.S. Pat. No. 5,478,328) and claimed herein, are designed to provide a compromise between "penetrating but dangerous" sharp needles of traditional systems and newer "safe but nonpenetrating" blunt cannulae of needleless blunt-cannula systems (described below). The inventive needles are designed to decrease the likelihood of harmful puncture of the skin of a healthcare worker (compared to that associated with a traditional needle) by one or both of the following:
  1) lessening the pointedness of the tip;
  2) providing one or more recessed orifices as opposed to an open tip;
(b) the "strong yet penetrable" diaphragms of the present disclosures are a compromise between the "strong but (relatively) impenetrable" and the "penetrable but weak" extremes described in the prior art (described below). They are designed to:
  1) provide an intact covering or plug with a section that, at the time of clinical use, can be pierced with greater penetrability than a conventional diaphragm (which requires penetration by a traditional "penetrating but dangerous" sharp-tip needle);
  2) have the integrity and long-term shelf-life approximate to that of a conventional diaphragm and thus maintain the sterility of the enclosed contents for months or years prior to the first clinical usage of the needle/diaphragm combination;
  3) have the versatility of a conventional diaphragm (i.e., be able to cover openings with a wide range of diameters as may be found on injection ports, bottle tops, etc.);
  4) provide a snug, secure fit for the needle or cannula which pierces it and thereby prevent leakage and dislodgement;
  5) provide resealing properties after needle or cannula removal that enable the diaphragm to maintain its integrity and hence the sterility of the underlying contents for a satisfactory duration.

Disclosure #II of the three-part series introduces the concept of and means of a "converting" mechanism for modifying the diaphragm immediately prior to its first penetration for clinical use. This converts a strong diaphragm which otherwise would not be so readily penetrable by a given "safe" needle or cannula to a diaphragm which can be used in combination with said needle or cannula.

Disclosure #III of the three-part series introduces the concept of and means of providing reversible compression of a prechannelled or preweakened diaphragm. This enables one to ensure effective closure of a preslit or preweakened region before a diaphragm has been penetrated by a needle or cannula and, in many embodiments, restoration of the ancillary pressure secures effective closure even after penetration.

As alluded to above, prior to the present invention, two extremes of needle/diaphragm combinations have been available: 1) Strong Diaphragm/ Dangerous Needle; or 2) Weak Diaphragm/Safe Cannula. These are described below:

1. Strong Diaphragm/Dangerous Needle —It traditionally was felt that, in virtually all settings, needle insertion through a diaphragm necessitated the use of a sharp needle. Known hypodermic needles for use with penetrating diaphragms typically have:
  (a) a sharp point;
  (b) an open tip. Such needles have cutting points, formed by a beveled cut typically at an angle of approximately 45° (or more) to the longitudinal axis of the needle shaft with an opening created at the junction of the beveled edge and the needle bore. Unfortunately, these features pose a threat to anyone who comes into contact with a used needle. The sharp point increases the likelihood of skin puncture; as evidenced by the large number of injuries, relatively little force is needed to penetrate the skin during an inadvertent stick with a sharp needle. The open tip can house infected fluid or tissue (herein called an inoculum); this increases the likelihood that a needle stick will result in disease transmission. The sharp-point, open-tip construction not only increases the risk of injury to a healthcare worker during usage but also increases the likelihood of accidental injury during recapping as a consequence of missing the cap or actually piercing the side of the cap.

2) Weak Diaphragm/Safe Cannula —The newly designed "needleless" blunt-cannula systems (e.g., the InterLink System, Baxter Healthcare Corp., Deerfield, Ill. in collaboration with Becton-Dickinson Co., Franklin Lakes N.J.; and the Lifeshields system, Abbott Laboratories, Abbott Park Ill.) contain a diaphragm that is modified at the time of manufacture to such a degree that it is penetrable by an "absolutely" blunt-tipped cannula (with an end that typically is 0° (flat) or hemispherical, and never with >15° angle to the longitudinal axis of the cannula shaft). The manufacture of the diaphragm (herein called a "blunt-cannula diaphragm") has been taught within the prior decade as follows:

(a) cutting a slit into the central portion of the diaphragm with a knife ("preslitting") (Jepson, Dudaran, and Finley WO89/06553 & WO90/11108 in 1989/90 —Baxter).

(b) reinforcing such a preslit diaphragm by covering the main plug with a thin diaphragm portion and using a metal ferrule which remains permanently in place for securing the inner and outer members of the stopper assembly together (Hook U.S. Pat. No. 5,328,041 in 1994 —Abbott). In justifying the need for his more complex process (which includes two stopper members and a ferrule), the inventor stated that this was required to maintain sterility of the contents of vials covered with a preslit diaphragm: "the same prepierced construction used in prepierced reseals cannot be implemented for the stoppers on vials because of sterility and shelf-life degradation questions."

(c) molding the diaphragm in two pieces which are joined by a penetrable hinged region (Grabenkort U.S. Pat. No. 5,403,293 in 1995 —Abbott). Although Grabenkort claimed that his method of "compression molding allows the tolerances at the hinged region to be better controlled than the alternate method of cutting a slit into a rubber diaphragm (as originally described in a patent assigned to Baxter), the procedure to accomplish this appears to be more complicated as it involves the production of a stiff annular collar having a first and second annular flange.

(d) using ultrasonic heating to create a weakened portion that extends at least partially through the diaphragm's midsection. The horn and anvil of the mounting device conduct heat away from the outer surfaces, thereby allowing them to remain continuous and unbroken (Helgren U.S. Pat. No. 5,403,525 in 1995 —Abbott).

Review of the earlier prior art shows that the use of a more readily penetrable diaphragm was taught 30 years previously, but none of the inventions of the prior art was designed to facilitate passage of a "safe" needle as described in the present invention. Wimmer (U.S. Pat. No. 3,653,528) taught a means of creating an indentation in the outer surface to facilitate piercing without coring by a standard hypodermic needle. Sandhage (U.S. Pat. No. 2,906,423 in 1959) described a preslit diaphragm which was puncturable by a round-tip plastic "needle" which was so blunt that it was also able to be inserted into the teat of a cow to inject medication for the treatment of mastitis; however, this required lubricant to "fill up the cut slit" after needle entry "to aid in preventing the entry of contaminant organisms." Ogle (U.S. Pat. No. 5,060,812) described diaphragms which were modified to such a degree that they were penetrable by a syringe tip or nozzle (as opposed to a needle or cannula). Garrett (U.S. Pat. No. 4,197,848 in 1980) described a resilient, impermeable membrane for a urinary irrigation system, wherein said membrane had a normally closed, resiliently deformable slit. Said slit was maintained closed by compression, but was penetrable by the blunt end of a syringe. Baxter, the assignee of that invention, noted in a subsequent disclosure (WO 90/11103) that there was still a need for a preslit injection site which "will reliably reseal . . . ."

Although the blunt-cannula diaphragms of the Baxter and Abbott needleless systems tend to self-seal after blunt cannula insertion, they do not guarantee adequate shelf-life and sterility in all contexts:

a) Because they require an appreciable degree of prechannelling or weakening at the time of manufacture, they have not been recommended for prolonged drug storage even prior to first clinical use and especially after they have been penetrated by a needle or cannula. Even in the prior art configuration in which the preslit extends only partway through the blunt-cannula diaphragm, "the end of the blunt cannula will be used to tear through the remainder of the sealing member." (WO 90/11103) This necessitates a very weak "tearable" portion which may restrict shelf-life, and it leads to the potential for poor resealing as a result of the tearing process. This has led to modifications such as the two stopper members and ferrule described above (Hooks U.S. Pat. No. 5,328,041) or an extra valve which serves to reinforce the potentially incompetent site of needle/cannula entry and thereby reduce the risk of leakage (Brimhall U.S. Pat. No. 5,242,393). Despite these modifications, bottles and bags that either house or transfer medication and/or fluids for extended periods of time typically are not equipped for use with the Baxter or Abbott blunt-cannula systems.

b) It is recommended that such blunt-cannula diaphragms be used only with specially designed blunt cannulae since they are prone to damage by sharp needles. Said cannulae have been described as having distal ends which are completely blunt (0° degree angle to the longitudinal axis), arcuate, or hemispherical or as having a lead post which extends beyond the end of the cannula (to guide insertion) or a taper with up to a 15° angle to the longitudinal axis. Greater tapers and actual points were avoided in large part because of the preslit/ preweakened diaphragm's susceptibility to damage. The inventors of needleless systems also proposed the use of conventional lubricant "to further reduce the friction and lower the insertion force required." (WO 90/11103)

c) The blunt-cannula diaphragms only can accept blunt cannulae of limited diameter and the diaphragm itself cannot be provided in the widths required to cover variously sized bottle tops, injection ports, and collection tubes without unacceptably compromising diaphragm integrity. As stated by the inventors (WO 90/11103) of the blunt-cannula system: "To provide for leak-free insertion, the length of the slit in the sealing member must be less than one-half the circumference of the cannula being inserted therethrough [—as a consequence of the greater penetrating ability of our inventive needles, the length of the slit would not so severely limit the diameter of the fluid channel when the proposed inventive needles are used] . . . In addition, the slit length must be great enough, given the elastic limit of the sealing member, to prevent tearing during insertion."[— again, this should be less of a problem when a more tapered device (e.g., inventive needle) is used].

d) In order to accommodate a blunt cannula, the preslit typically extends to the surface or an indentation is produced so as to facilitate blunt cannula insertion. Either of these surface modifications may limit the effectiveness of antiseptic swabbing. Attempts to overcome this problem have entailed the addition of a potentially costly step in the manufacturing process, including covering the preslit stopper with a second member (which is to be torn by the blunt cannula).

The absolutely blunt cannulae of the Baxter and Abbott needleless systems also pose limitations. As stated above, they can be of only limited diameter (and thus can allow only limited flow rates) as they would otherwise require an unacceptably large slit in the diaphragm to allow insertion of their blunt tip. In addition, they tend to slip out of the blunt-cannula diaphragm, a problem that could be partially mitigated by increasing cannula length, but such a change would slow flow even further. Realizing the potential problems associated with a standard blunt cannula system, the inventors (WO 90/11103) note: "In accordance with further aspects of this invention, the blunt cannula may be provided with features that facilitate insertion into the injection site, enhance fluid flow or dispersion, increase tug resistance, and reduce kickback." These include: 1) the inclusion of a plurality of elongate discharge slits to improve flow which otherwise may be compromised by the cannula's narrow diameter as well as to decrease the contact surface area so as to facilitate insertion; 2) grooves on the side of the cannula to reduce surface area; 3) a lead post to guide cannula insertion; 4) annular barbs to reduce kickback; 5) matching locking means, gripping means, and "retaining fingers" to secure engagement. Moreover, the use of blunt cannulae necessitates modification or replacement of existing setups, so that a blunt-cannula diaphragm is always available. The use of the prior art blunt cannula in the absence of a setup with a preslit or weakened diaphragm is virtually impossible unless one inserts a special "spike" adaptor. One side of the adaptor has a sharply pointed, open-tipped spike which can pierce a standard diaphragm; the other side has a preslit diaphragm. The spike must remain in place as long as the blunt cannula is used; and it must be discarded as a potentially hazardous sharp object (akin to a "penetrating but dangerous" needle) once it is no longer required. To the best of our knowledge, there has been no attempt to increase cannula penetrating properties in a manner comparable to that of the present disclosure; i.e., there has been no obvious attempt to increase penetrating capabilities by using a tapered needle (such as those claimed in the present three-part series) and thereby allowing for an inherently stronger entry point in the diaphragm.

The limitations of needleless systems are significant to the degree that the New York State Study on Needlestick Prevention Devices (in 1992) reported that two-thirds of healthcare workers felt that special training in the use of a needleless device was required and 20.3% of the workers at a major test center believed delivery was impeded with the device. Furthermore, the report noted that, because of the inability to provide blunt- cannula diaphragms for most containers (e.g. bottles, bags), ". . . needles used with the system continued to be a hazard for injury. In one institution, needles continued to be used for administering heparin or saline 'flushes' while in the other hospital, in an attempt to avoid this hazard, a complicated system using multiple components was put into place." These factors led the compilers of the NYS report to conclude that blunt-cannula systems are less cost-effective than systems using traditional sharp, open-tipped needles enclosed in a plastic shield; thus, although they do not eliminate the potential to contact a dangerous needle, the report concluded that shielded needle systems produce "greater reductions in needlestick injuries" than the needleless systems. Of note, neither the NYS Study nor an Apr. 16, 1992 FDA Safety Alert ("Needlestick and other risks from hypodermic needles on secondary i.v. administration sets") recommended or even mentioned the use of an intrinsically safer needle (as opposed to a "safe but nonpenetrating" blunt cannula or a "penetrating but dangerous" sharp needle which is extrinsically modified with a shield). This provides strong evidence that the subject-matter disclosed herein, and in the applications and patents incorporated by reference, was not apparent even to experts and leaders in this field.

SUMMARY OF THE INVENTION

The present invention is #I of a three-part series of disclosures describing "Strong Diaphragm/Safe Needle" systems and the design and use of their individual components in order to bridge the gap between the Strong Diaphragm/Dangerous Needle and Weak Diaphragm/Safe Cannula extremes of the prior art. An important advantage of the present inventions is that, in contrast to the prior art, they provide healthcare worker safety while maintaining diaphragm integrity; i.e., the inventive series of needles and diaphragms avoid the need for diaphragms which are compromised to the point of having suboptimal sealing and unacceptably short shelf-lives as well as avoiding the need for sharp, open-tipped hypodermic needles or spike adaptors that pose infectious risks to healthcare workers. In most embodiments of the present disclosure, needle configurations which have not previously been recommended for diaphragm penetration (except for the suggestion of such in the inventors' original patent, U.S. Pat. No. 5,478,328 in 1995) are employed. They pose far less risk to healthcare workers than standard hypodermic needles and can be matched with diaphragms to optimize needle/diaphragm efficiency and versatility.

Disclosures #II and #III of this series entail the use of an additional step: #II involves penetration by a "convertor" to provide a suitable channel for safe needle or blunt cannula insertion; #III involves the reversible application of enhanced compressive pressure in order to decrease diaphragm permeability. In contrast, the present disclosure employs inventive needles and diaphragms and needle/diaphragm combinations to achieve these goals.

By utilizing the inventive needles as opposed to blunt cannulae, the present invention allows for maintenance of a smaller diaphragm opening and/or a lesser degree of diaphragm weakening. This substantially prevents unwanted communication between contents and environs, allows the inventive diaphragm to remain suitable for repeated use with regular as well as inventive needles (thereby obviating the need for multiple sets of supplies and bulky adaptors), and allows the inventive diaphragms to be constructed in a wide range of sizes (which may be adapted to meet medical needs without requiring a spike adaptor or standard sharp needle or the need for multiple stopper layers and leak-preventing valves).

The intrinsically safer inventive needles —which are far more versatile than the blunt cannulae of needleless systems —are achieved by customizing needles with one or both of the following:

(a) a partially blunted "safe" tip which is sharp enough to puncture the inventive diaphragm but not sharp enough to penetrate the skin under normal clinical conditions, including incidental contact or contact during recapping;

(b) a closed tip and one or more recessed orifices to minimize exposure to a sizable inoculum should superficial skin penetration occur. The increased safety afforded by the closed tip allows for the safe use of needles which are significantly more pointed than the blunt cannula of needleless systems and thus usable with a wider range of diaphragms and in a wider range of lengths and diameters. In addition, the solid tip lacks the "cutting" quality of an open-tip design and thereby should allow for more effective leak-free engagement and resealing. Moreover, to date, all reported transmissions of AIDS via puncture wounds to healthcare workers have resulted from puncture with a hollow bore device such as a traditional hypodermic needle or a broken glass tube. These present a sizeable inoculum which may be avoided with the solid-tip needles described herein.

Solid-tip needles are commercially available from many manufacturers for a variety of uses, including: spinal myelography, injection of intraspinal anesthetics, soft tissue biopsy, and perineural injections, as summarized by the present inventors in U.S. Pat. No. 5,478,328 in 1995 in which we taught that the use of a recessed-orifice needle permits the use of catheters which can be rotated to selectively overlie the needle orifice(s). No other inventor or manufacturer has even proposed the use of the recessed-orifice configuration for the purpose of healthcare worker safety, including the inventors of the following patents (U.S. unless noted otherwise): Leiter U.S. Pat. No. 145,217; Mitchell and Gillespie 561,059; Gillman 1,526,595; Weyl 446,818 (German); Peterson 2,097,039; Hanson 2,634,726; Gewecke 2,862,495; Morgan 1,196,601 (French); Schofield 3,181,336; Guttman 3,509,880; Jamshidi 3,882,849; Choksi 4,058,121; Sampson 4,190,048; Galindo 4,411,657; Guttman 4,413,993; Johnson 4,710,180; Sprotte 3,020,926 (German); Foran 4,767,407. These references disclose one or more of the following objectives: (1) to avoid coring of a rubber diaphragm by an open-bevel needle; (2) to minimize trauma to a patient's tissues; (3) to decrease the likelihood of harmful intraneural injections during infiltration with local anesthetic; (4) to provide an additional orifice to allow venting; (5) to provide a special needle hub; and (6) to improve the success of intravenous cannulation. For example, Hanson (U.S. Pat. No. 2,634,726) discloses a needle with a chisel-like point and a single recessed orifice which opens obliquely on the side of the shaft ipsilateral of the convex side of the needle point and is said to minimize the likelihood of clogging the needle and injecting a cork or rubber core into a patient. In 1983, Galindo (U.S. Pat. No. 4,411,657) disclosed a needle with a solid tapered tip and recessed orifice introduced to decrease nerve trauma during injection of local anesthetic. In that same year, Guttman (U.S. Pat. No. 4,413,993) claimed his recessed-orifice needle for minimizing infiltration from the cannulated vessel during intravenous infusion of fluid (even if the tip of the needle extended beyond the back wall of the vessel). In 1985, Alchas (U.S. Pat. No. 4,537,593) introduced a recessed-orifice needle with an overlying sleeve to allow venting during transfer of liquid to or from a container. In 1987, Johnson (U.S. Pat. No. 4,710,180) described a blunt-tipped cannula with multiple recessed orifices for injecting fat cells into the skin after an incision was made to allow cannula insertion. Germany No. 3,020,926 introduced a modified recessed-orifice needle for spinal anesthesia with improved flow characteristics and a lesser incidence of dural tear and postspinal headache.

Thus, the present disclosure teaches new needle/diaphragm combinations with needle designs which not only are obviously different from standard hypodermic needles but also differ significantly from those for the Baxter and Abbott needleless systems described above.

This disclosure also teaches a combined testing procedure which addresses both testing of diaphragm integrity and penetrability as well as relative needle safety using a combined index (described below).

A further feature of the invention is to provide a needle and diaphragm combination which is amenable to user friendly, efficient external modifications to decrease the likelihood of healthcare worker exposure to contaminated fluids even in the absence of a needle stick —e.g., retractable caps and sheaths, including recessed-orifice needles covered by sheaths or caps as disclosed in the applicant's U.S. Pat. No. 5,478,328, incorporated by reference.

BRIEF DESCRIPTION OF THE DRAWINGS

In FIG. 8c, an optional depression identifies the site for insertion of a convertor and/or needle and facilitates such insertion. FIG. 8d shows an optional depression surrounded by a circumferential ridge.

FIG. 11a shows that the rim 7 around the diaphragm and its housing may be configured to provide increased axial compressive pressure and thereby help to maintain diaphragm integrity. FIG. 11b shows that the entire diaphragm or simply the region which included the prechannelled or preweakened site may be made of increased thickness to maintain diaphragm integrity. FIGS. 11c–11d illustrate the presence of an additional membrane which may itself have a slit or simply provide additional thickness. FIG. 11e is another embodiment which illustrates a way to minimize the effect of prechannelling (or preweakening) on diaphragm integrity; increased compressive force is provided by a tight-fitting band. The band may remain permanently in place or, as described in Disclosure #III, it may be removed to partially relieve the compressive forces prior to clinical use.

c) closed tapered tip with a rounded distal end; d) closed tapered tip with a flat distal end.

Figure 16:
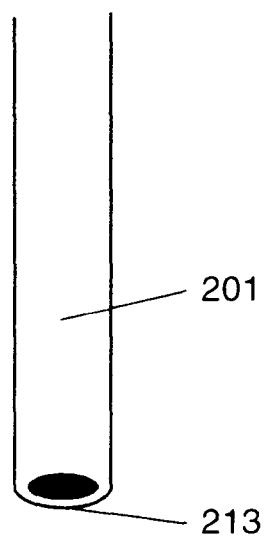
Figure 18A:
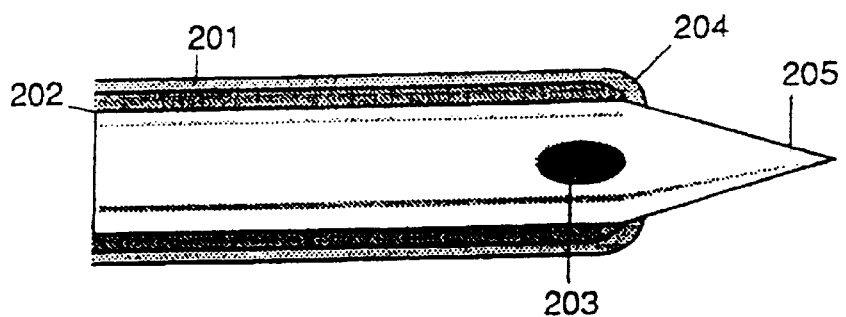
Figure 18B:
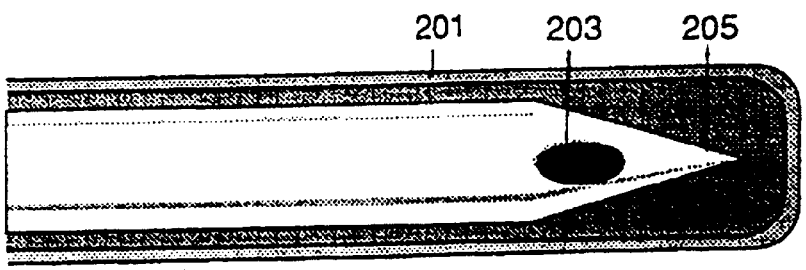
Figure 18C:
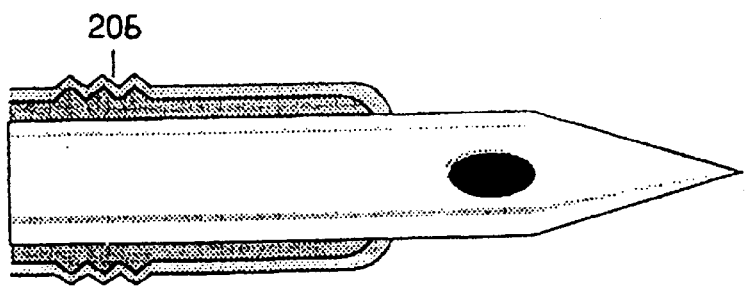
Figure 18D:
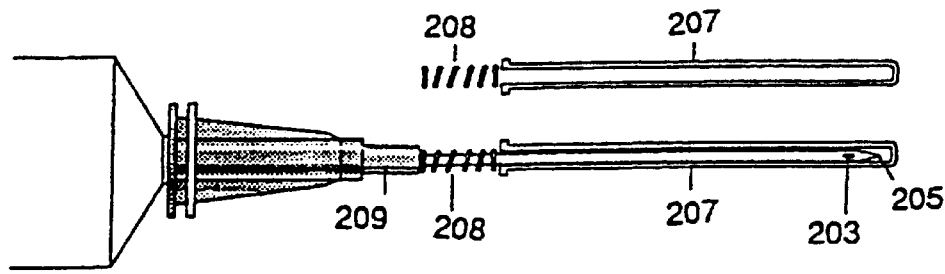
Figure 18E:
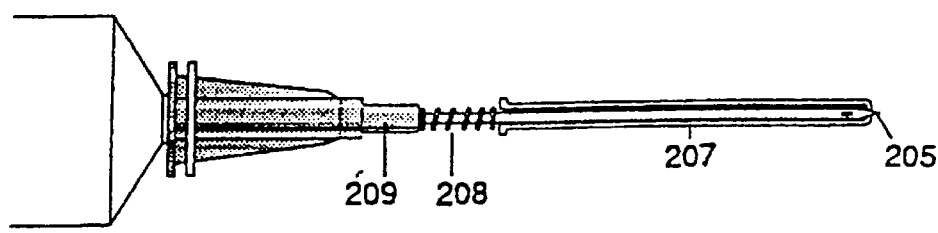
Figure 18F:
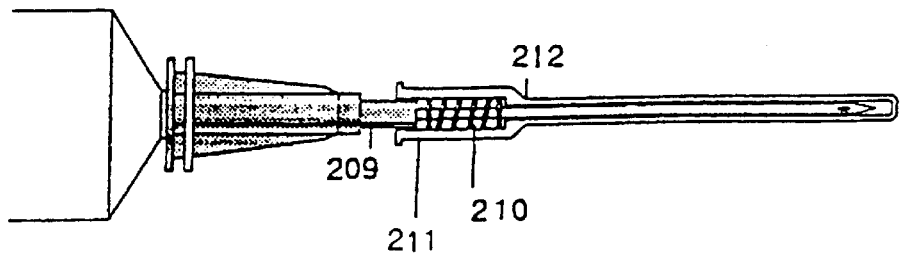
Figure 19A:
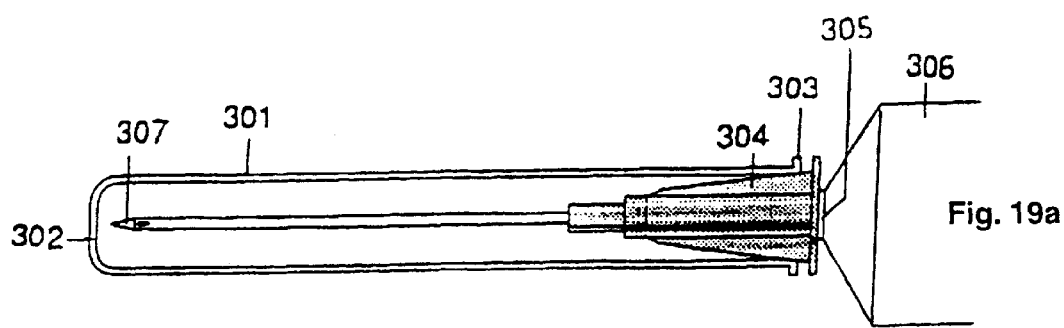
Figure 19B:
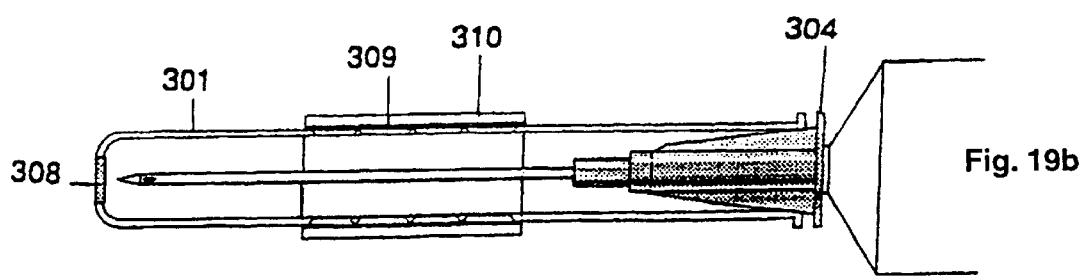
Figure 19C:
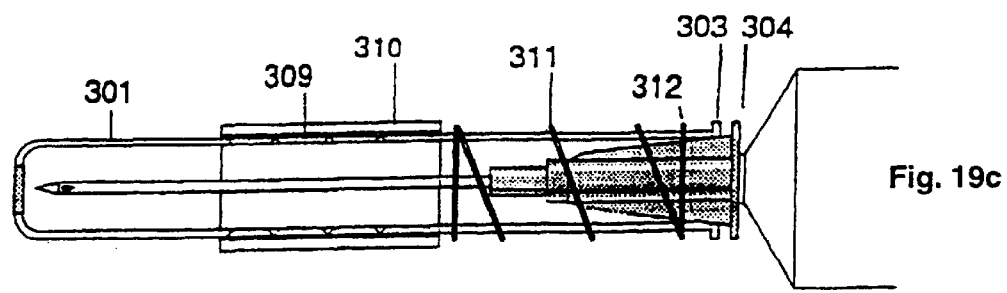
Figure 19D:
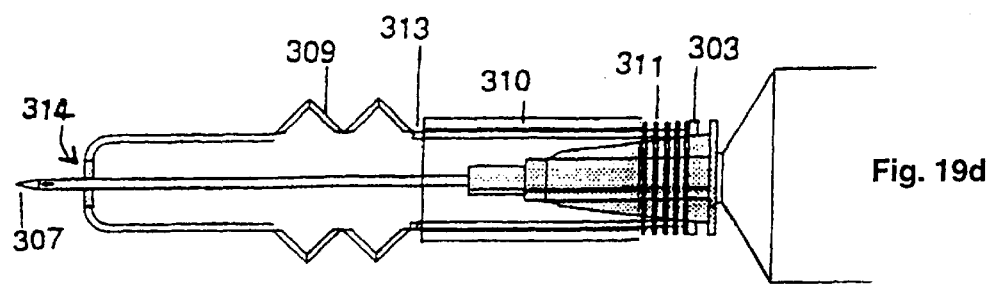
Figure 19E:
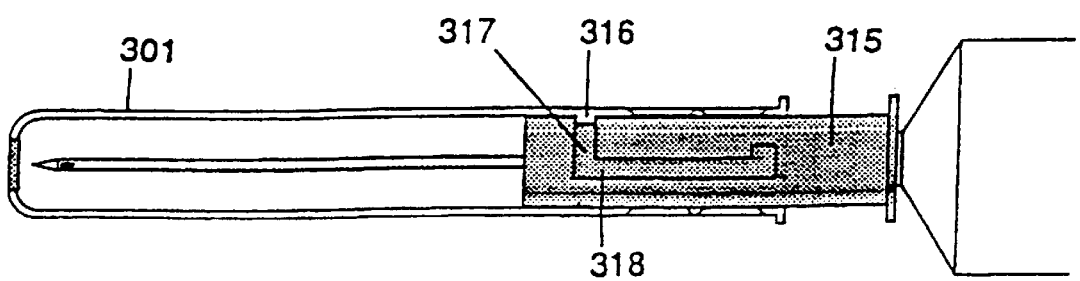
Figure 19F:
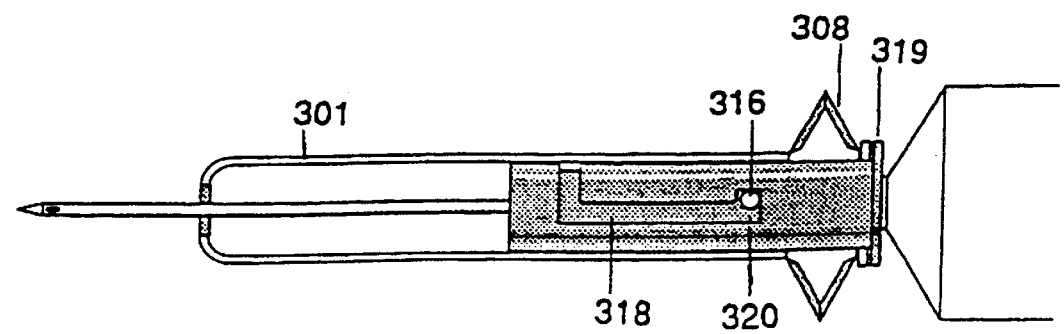
Figure 19G:
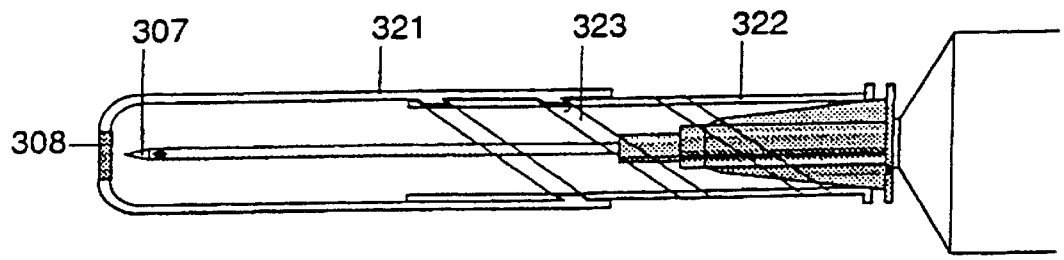
Figure 19H:
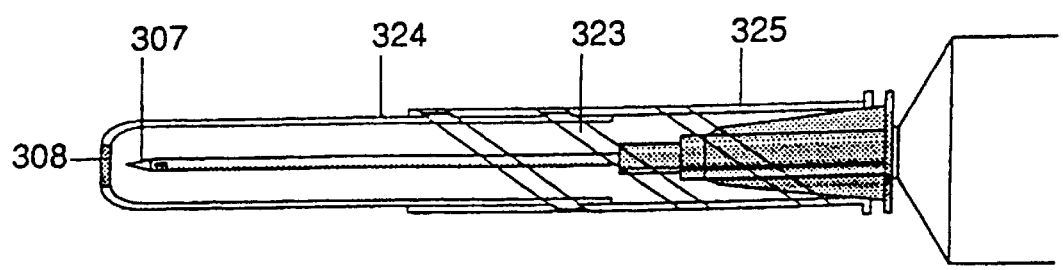

FIG. 16 shows an "absolutely" blunt cannula, consistent with that shown for needleless systems in the prior art. (This requires a larger opening—e.g., a bigger slit—than a tapered inventive needle.

FIGS. 17a–17p are schematic diagrams showing sixteen needles which illustrate some of the many potential orientations of channels and recessed orifices in embodiments of the present invention that may be adapted for specific needle/diaphragm combinations. Each of the examples includes a tapered region (with an angle greater than about 15°) which leads to a solid partially blunted tip and recessed orifice(s) along the shaft and/or the tapered region of the needle.

FIGS. 18a–18f show embodiments of needles with retractable sheaths which are shown in FIGS. 11a–11c and 12a–12c and described at col. 12, lines 41 –col. 13, line 67 in U.S. Pat. No. 5,478,328, incorporated by reference, and are considered to be aspects of the present invention.

FIGS. 19a–19h show embodiments of needles with needle caps which are shown in FIGS. 13a–13d, 14a–14b and 15a–15b and described at col. 14, lines 1–col. 15, line 63 in U.S. Pat. No. 5,478,328, incorporated by reference, and are considered to be aspects of the present invention.

Figure 20A:
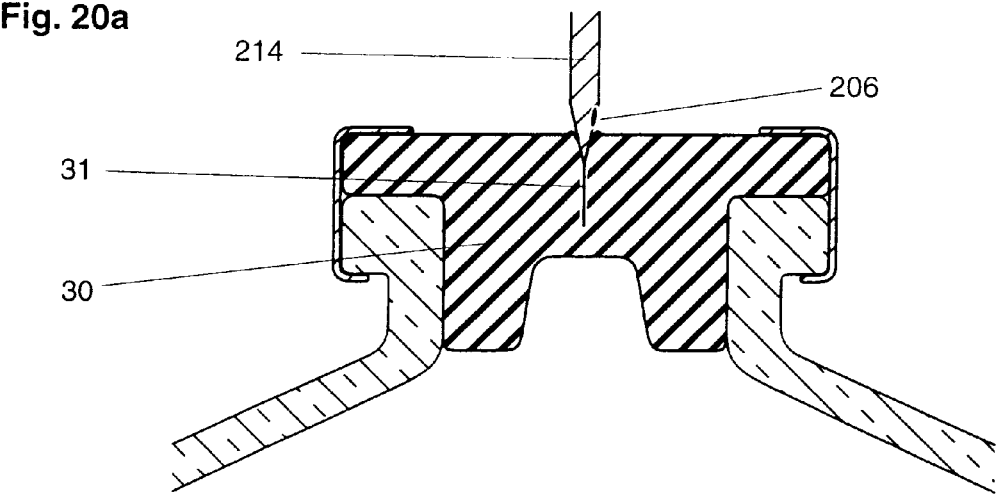
Figure 20B:
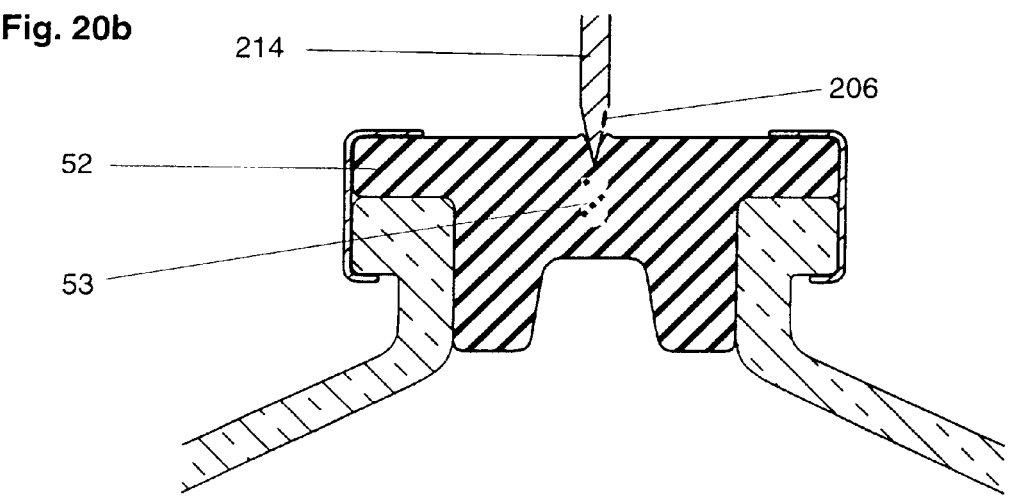

FIGS. 20a and 20b show combinations of an embodiment of an inventive needle with a matched diaphragm which has undergone prechannelling and/or preweakening prior to needle insertion: a) diaphragm with a slit; b) diaphragm with a preweakened region.

Figure 21:
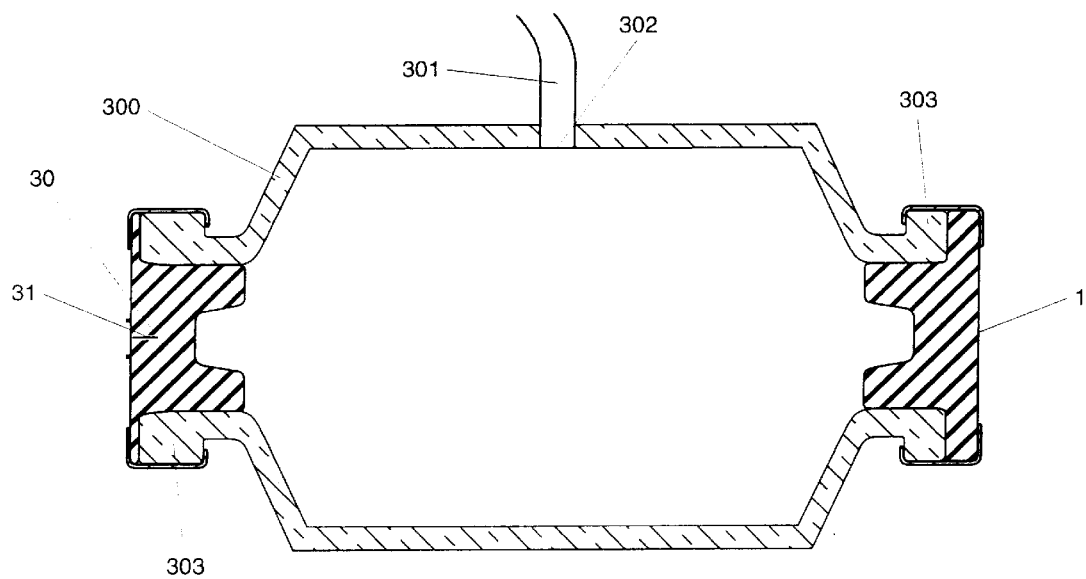

FIG. 21 shows an example of an arrangement to simultaneously test and compare two or more diaphragms with respect to their leak-free integrity in the face of different pressures. The internal pressures may be increased by infusing fluid through a separate port.

Figure 22A:
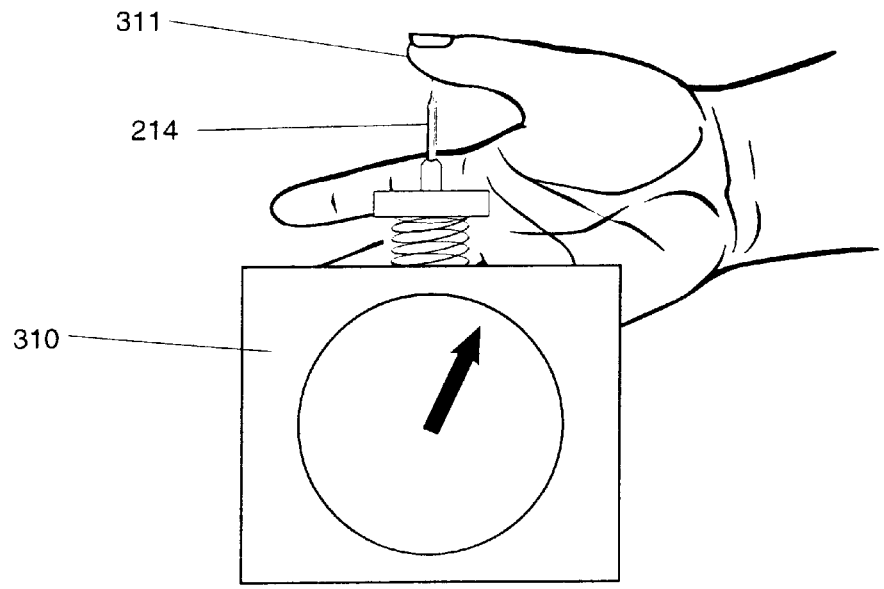
Figure 22B:
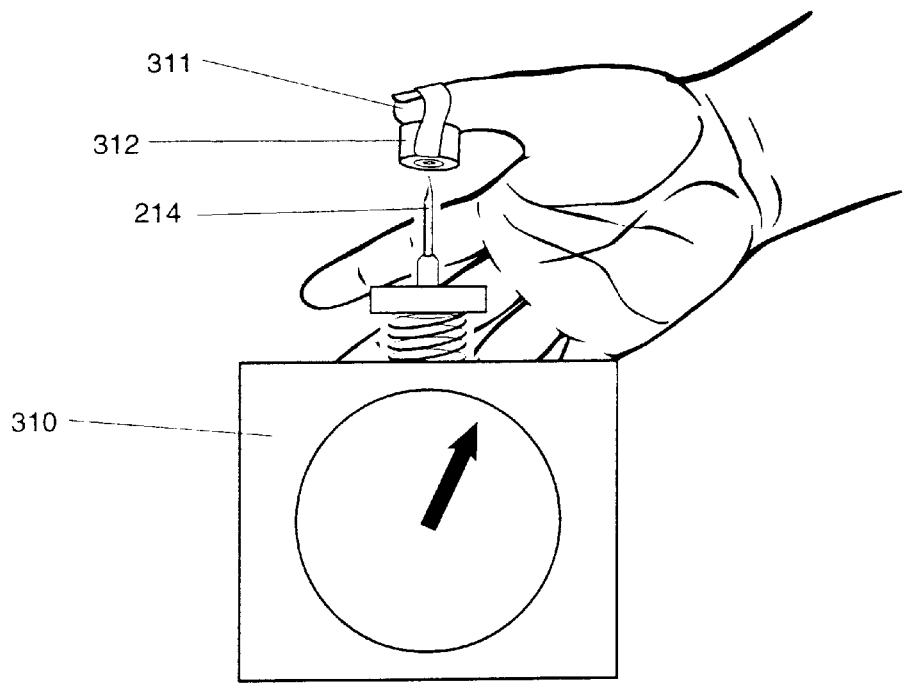

FIGS. 22a and 22b illustrate an arrangement for determining the force required for a given needle to penetrate the skin (FIG. 22a) or a diaphragm (FIG. 22b) wherein the needle is mounted on a scale which records the force required for penetration.

Figure 23A:
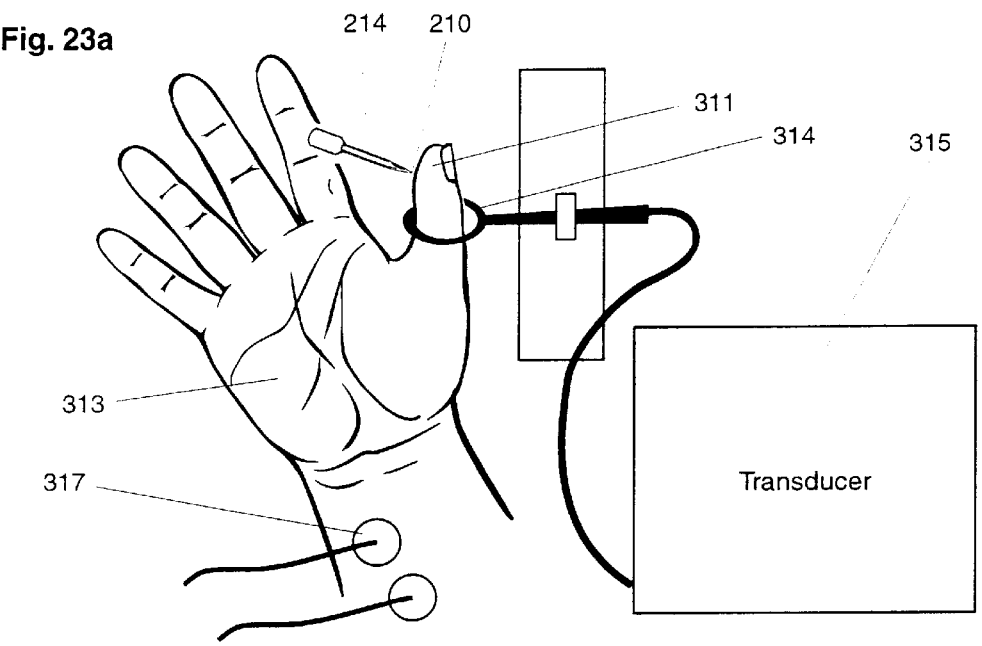
Figure 23B:
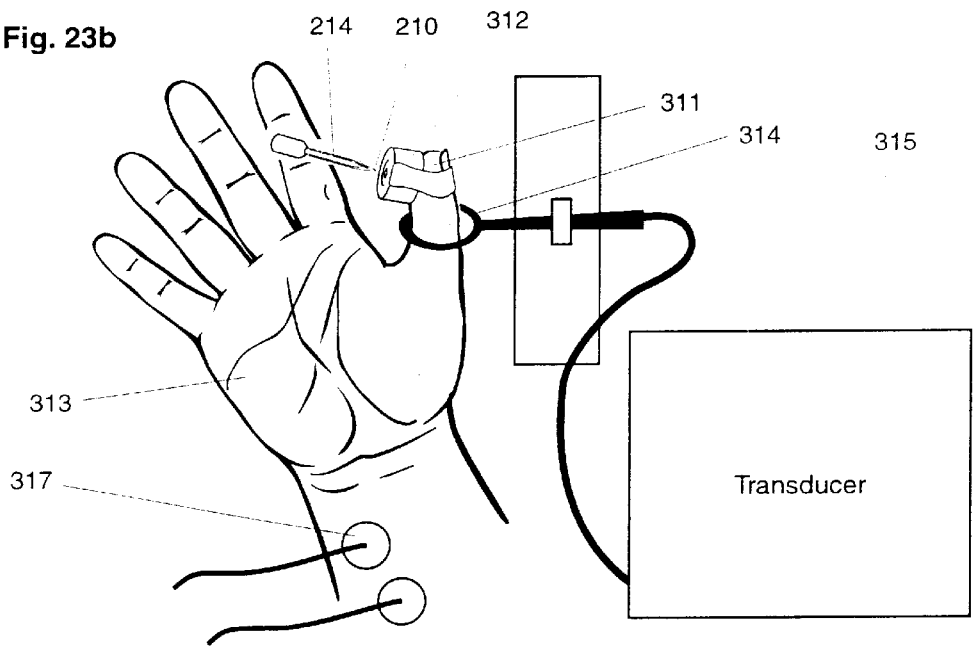

FIGS. 23a and 23b illustrate a more elaborate arrangement for testing the penetrability skin and diaphragms. The illustrated mechanism is designed to provide involuntary movements of the thumb by contraction of the adductor pollicis muscle as a result of stimulation of the ulnar nerve (analogous to the means used to assess neuromuscular weakness in patients undergoing general anesthesia). The force of contraction is recorded by a transducer (specifically an adductor pollicis force transducer). In the pictured embodiments, the needle is maintained in a fixed position in front of the thumb. In alternative embodiments, the needle can be secured to a thumb while the object to be punctured is maintained in a fixed position in front of it.

DETAILED DESCRIPTION OF EMBODIMENTS OF THE INVENTION

The following description of embodiments of the invention refers to the accompanying drawings. It will detail features of the diaphragms and safety needles of the inventive series. Other objects, features, and advantages of the present invention will become apparent from this description. It should be noted that we will not attempt to reteach aspects that already have been described in the prior art, such as the construction of a standard diaphragm, standard needle, or blunt cannula. It also should be noted that, although some of the individual components described in the present disclosure may in and of themselves not be unique, their use in combination has not heretofore been known. It should be evident that modifications, adaptations and equivalents of specific features and the combination of such features from the specific embodiments described below are intended to be within the spirit and scope of this disclosure.

The diaphragms of the present invention are designed to:

a) maintain their integrity prior to clinical use;

b) be readily penetrable to inventive needles at the time of clinical use;

c) demonstrate desired leak-free engagement and sealability during and after such use. These goals are achieved with a series of inventive diaphragms which remain intact or undergo only slight compromise (preslitting or preweakening) prior to clinical use.

The diaphragm may be composed of a number of different materials. Soft, impermeable, easily penetrable, resilient materials are preferred so that the diaphragm: 1) provides effective, leak-free closure prior to needle insertion; 2) has the penetrability, resilience, and memory to allow efficient insertion of the desired needles or cannulae; 3) engages the needle effectively; and 4) has sufficient memory and resilience to reseal effectively. As noted by Sims in U.S. Pat. No. 4,846,809, diaphragms should be formed with sufficient memory so that an opening formed by a penetrating needle point will tend to close after the needle tip has been retracted beyond the membrane. Polyisoprene rubber is a preferred form of resealable rubber, although resealable latex, silicone or butyl rubber may be used. Brimhall (U.S. Pat. No. 5,242,393) has described the use of an elastically deformable thermoset elastomer, preferably Dow Corning Medical Grade Injection Moldable silicone rubber. Donnelly U.S. Pat. No. 4,513,651 teaches a stopper that is a composite inner elastomer core and an annular surround plastic cap. Grippi U.S. Pat. No. 4,697,717 describes a stopper that is a composite of plastic and rubber.

In each of the embodiments, the diaphragm is housed in a retaining member. This typically is a cylindrical housing, but it may take on other forms so long as it applies axially directed forces to the sealing member. Said cylindrical housing may be tapered at the top in order to promote sealing of this region and to provide a curved exterior peripheral surface under suitable pressure. Kleiner U.S. Pat. No. 2,607,347 (in 1952) taught that "By having the plug portion of slightly larger diameter than the bore which receives it, that portion is placed under compression as the stopper is positioned."

Figure 1:
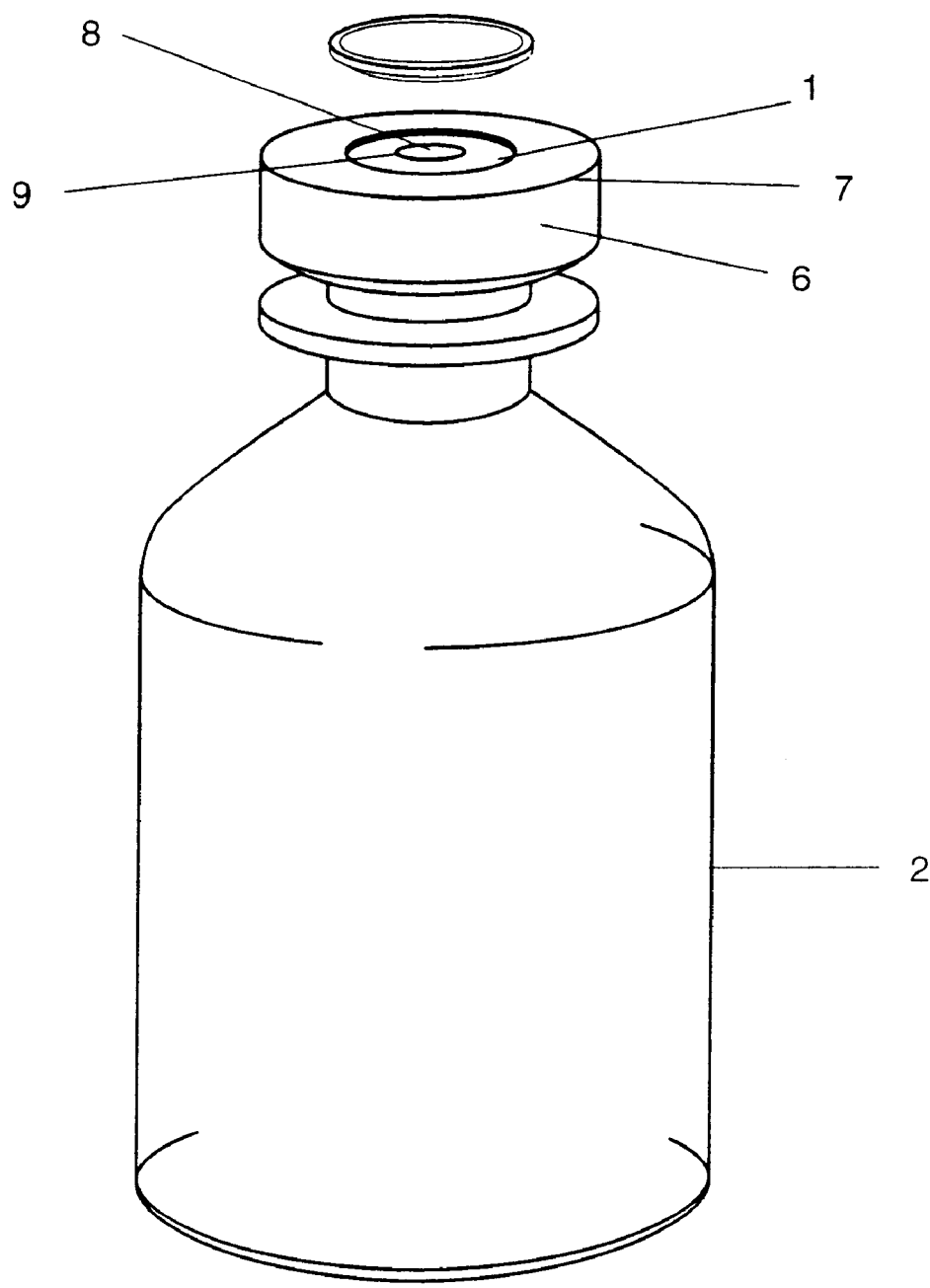
FIG. 1 shows a standard diaphragm on top of a typical medication vial.
Figure 2:
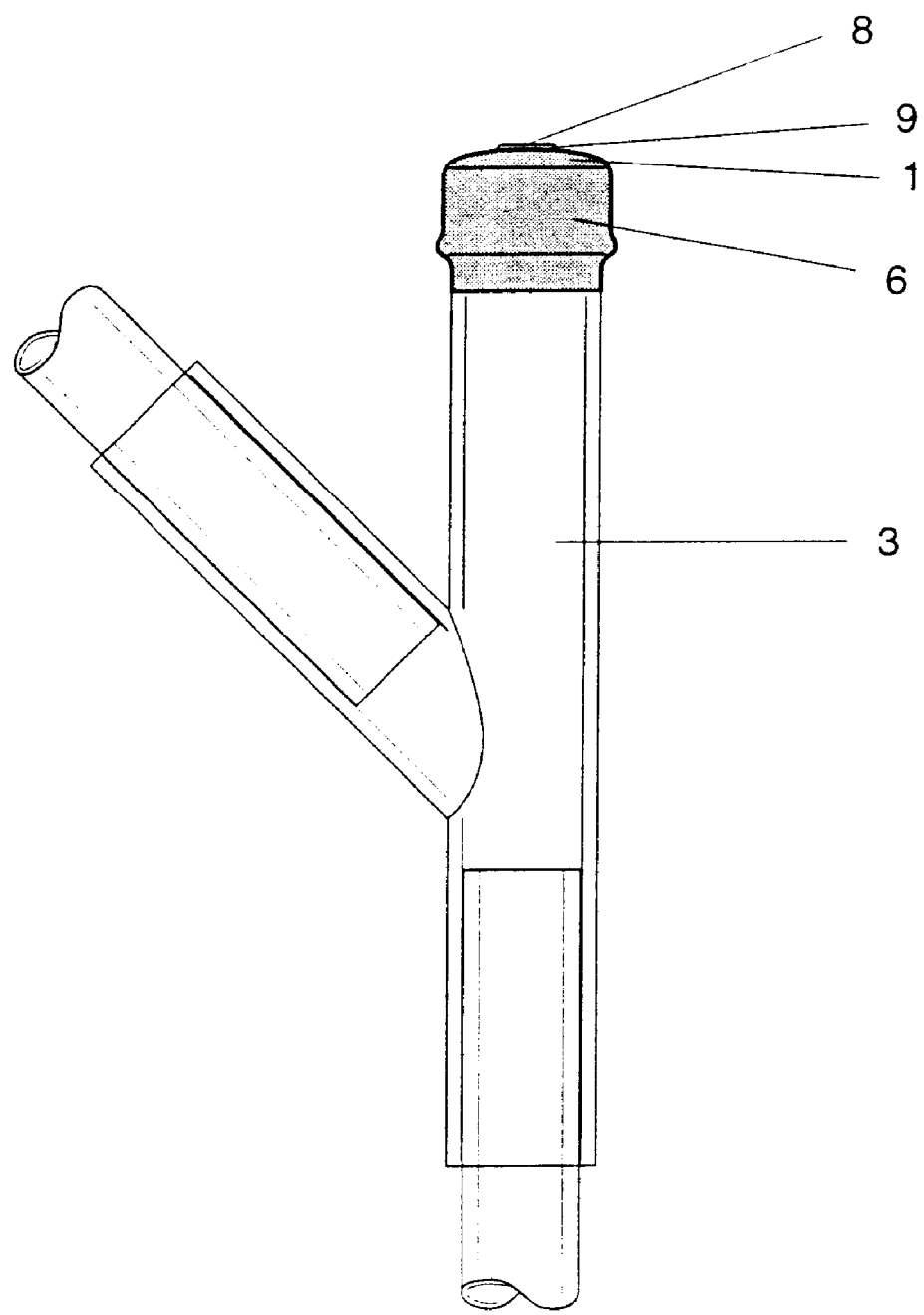
FIG. 2 shows a standard diaphragm on top of a standard injection port for intermittent infusion of medications and fluids via intravenous tubing which is connected to an indwelling intravenous catheter.
Figure 3:
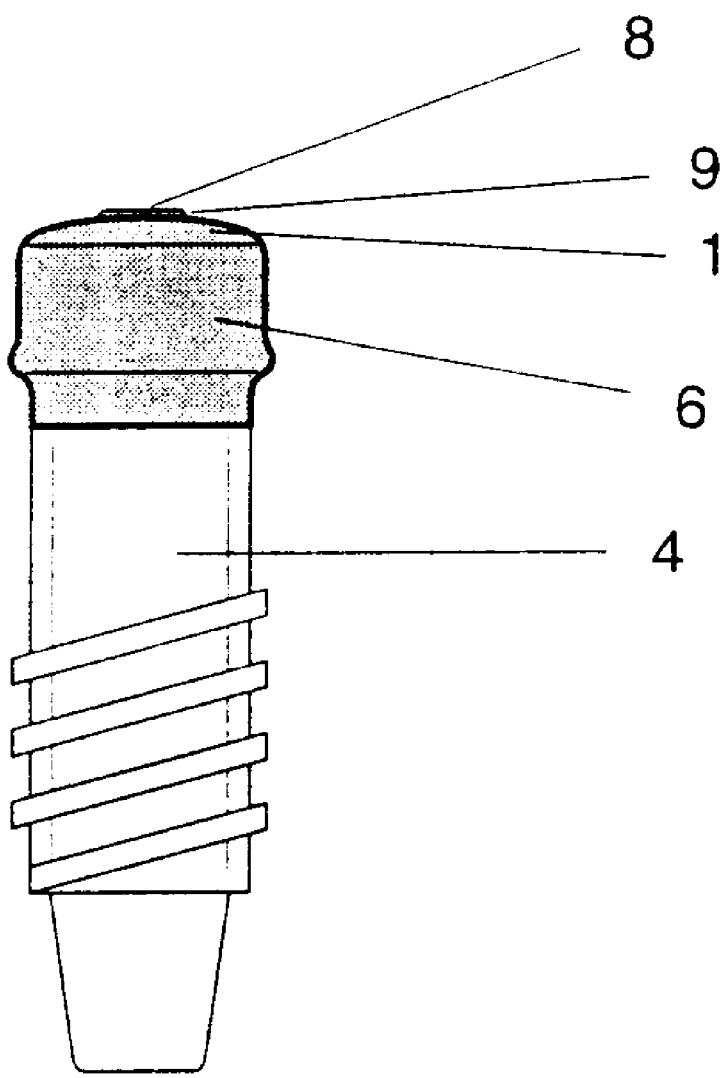
FIG. 3 shows a standard diaphragm on top of an adaptor for penetrable plugging of the nonpatient end of an indwelling catheter (e.g., a standard heparin lock for intermittent intravenous infusion of drugs).
Figure 4:
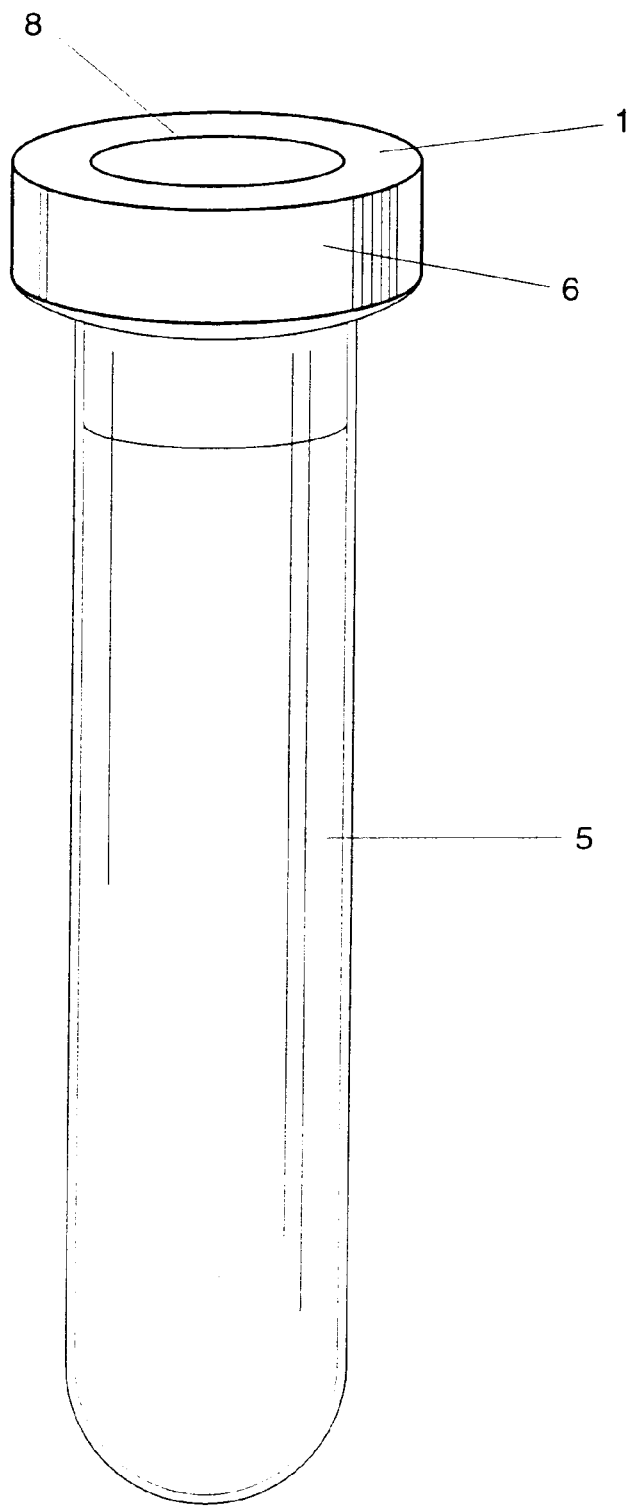
FIG. 4 shows a standard diaphragm on top of a standard vacuum tube for blood collection from a needle attached to a filled syringe or by attachment to a vacuutainer blood collection system.
Figure 5A:
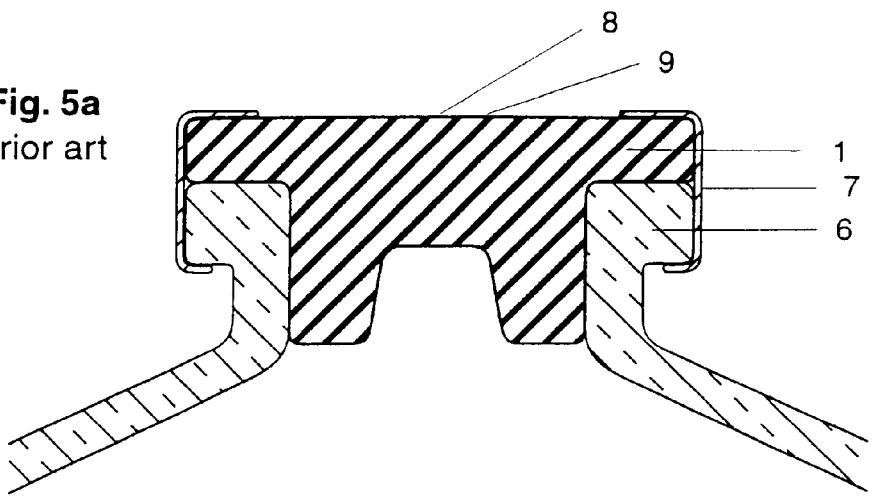
FIGS. 5a–5c are cross-sectional views of an intact (i.e., non-slit, non-weakened) compressible diaphragm which is maintained under compressive pressure in one of many potential housings, for example those in FIGS. 1–4 above.
Figure 5B:
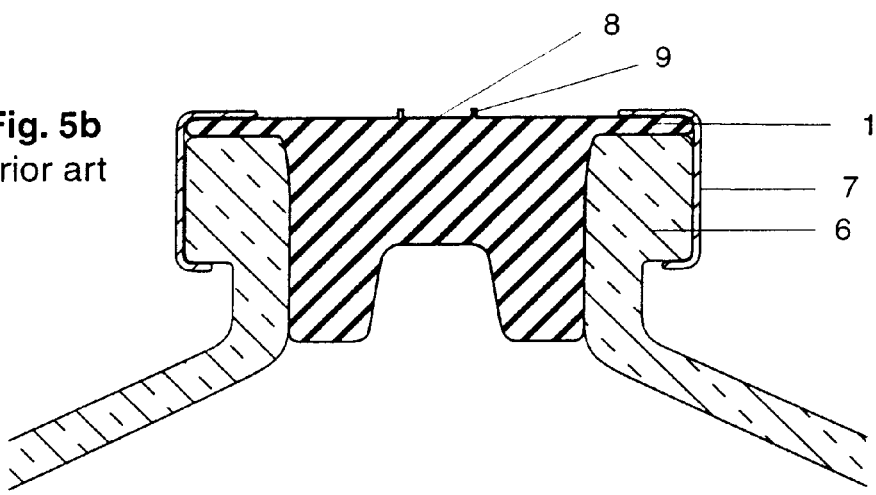
Figure 5C:
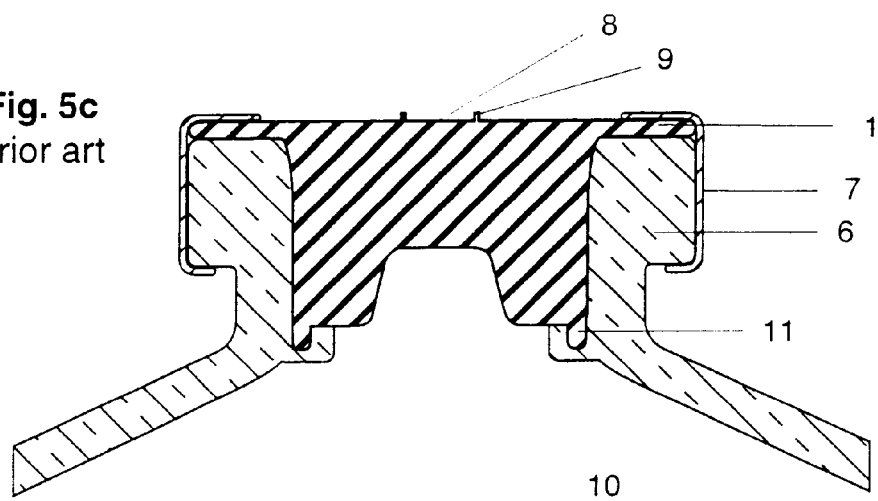

FIGS. 1–5 show standard diaphragms 1 as taught by the prior art, on top of a typical medication bottle 2, on an i.v. tubing injection port 3, on a heparin lock 4 for drug infusion, and on a vacuum tube 5 for blood collection. The receptacle 6 in which the diaphragm is retained provides for compressive engagement and retention. As illustrated in FIG. 5, the diaphragm 1 may extend to varying degrees (if at all) above the receptacle 6. Retention of the diaphragm may be augmented by a rim 7 around the circumferential surface of the diaphragm. Diaphragms typically have a "soft spot"8 which is surrounded by a raised border 9 (FIG. 5b). This is the preferred site for penetration with a standard hypodermic needle. The configuration of the portion of the housing below the receptacle will depend on the nature of the underlying structure (e.g., bottle vs. i.v. tubing injection port). This portion of the housing is also constructed so as to accommodate the displaced diaphragm when it is deformed by penetration by a needle or cannula. FIG. 5c shows a lip 10 in the housing which creates a channel 11 for this accommodation. (For purposes of simplicity, such a feature is not included in most of our illustrations of the prior art or of the present invention.)

Figure 6A:
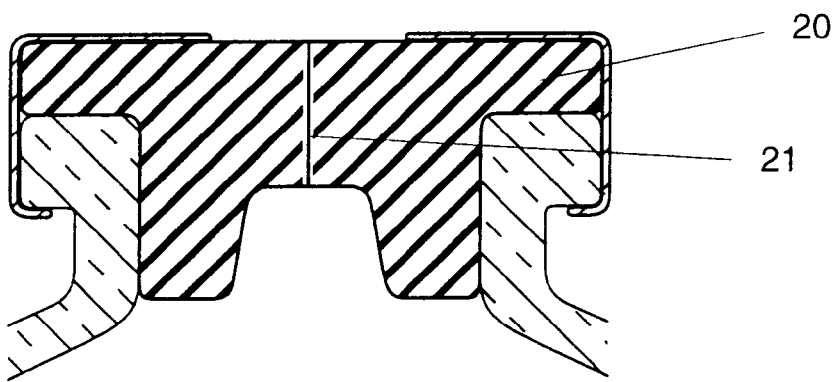
FIGS. 6a and 6b are cross-sectional views of different forms of preslit diaphragms that have been taught by the prior art, wherein the slit (which is imparted at the time of manufacture) extends all the way through or most of the way through the diaphragm.
Figure 6B:
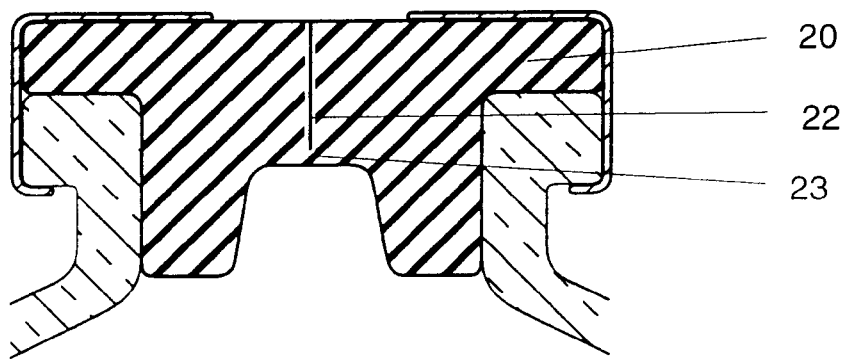
Figure 7A:
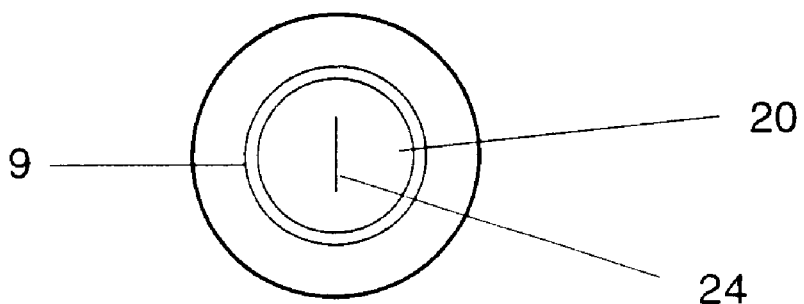
FIGS. 7a and 7b are top views of preslit diaphragms which illustrate slits as they appear in embodiments of the prior art.
Figure 7B:
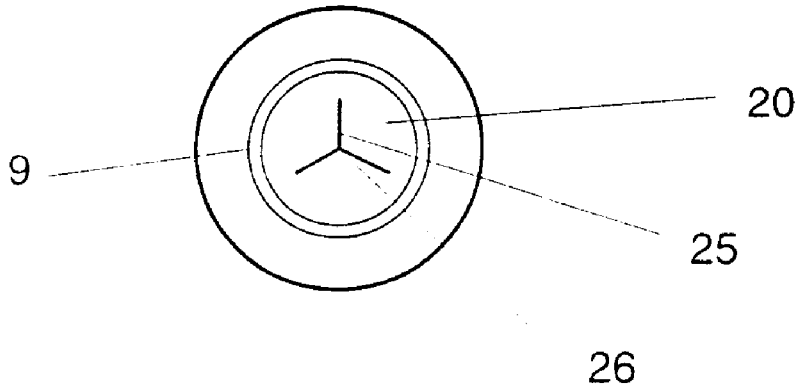
Figure 8A:
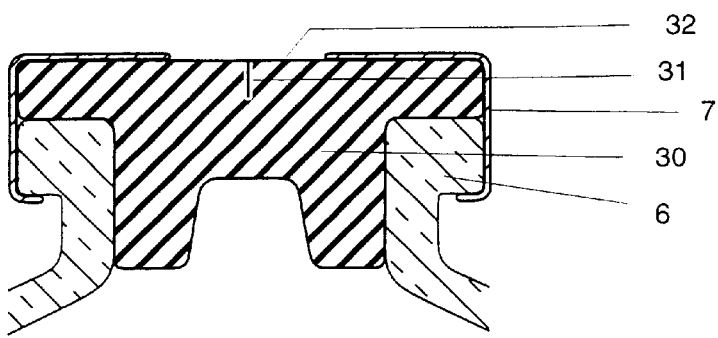
FIGS. 8a–8d are cross-sectional views of embodiments of the present invention wherein the diaphragm is preslit to a lesser degree than was required for subsequent blunt cannula penetration as taught by the prior art.
Figure 8B:
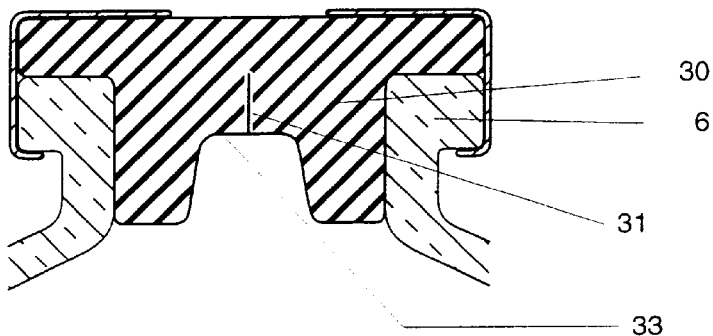
Figure 8C:
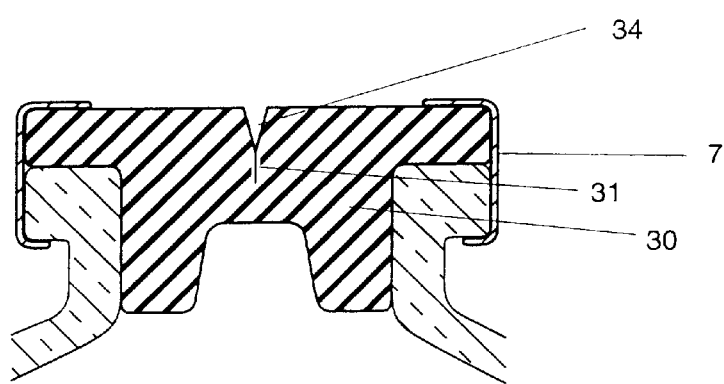
Figure 8D:
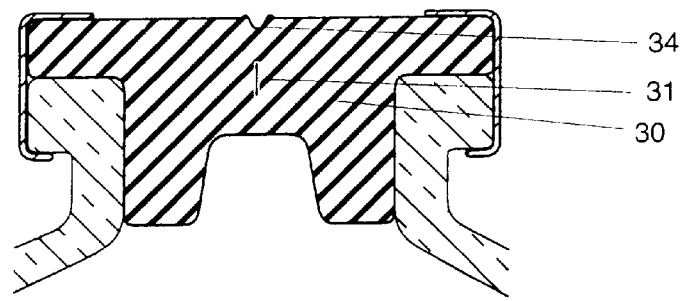

The prior art has shown that, for needleless systems, a diaphragm may be altered at the time of manufacture to allow penetration by a blunt cannula. FIGS. 6 and 7 show prior art diaphragms 20 which have been manufactured for penetration by a blunt cannula such that they contain a slit 21 which extends through the entire thickness of the diaphragm, or a slit 22 which extends substantially but not entirely therethrough, so as to leave a small tearable region 23. As shown in the top view (FIG. 7), the penetrable area may consist of a single slit 24 or an array of slits 25 such as the three-armed cut, the arms of which define a 120° angle 26 to each other.

The prior art taught the creation of a slit that was long enough, wide enough, and deep enough to allow insertion of a blunt cannula and to minimize the need for excessive force and increased risk of tearing. However, the size of the slits was limited by their ability to ensure effective leakfree engagement and subsequent resealing. WO 90/11103 taught that the length of the slit(s) should be <½ the circumference of the cannula being inserted therethrough. Such a requirement also limited the size of the cannula; i.e., a wide cannula would require a large slit and thus the integrity of the diaphragm would be compromised even before cannula insertion. The present invention makes it possible to avoid these limitations, and thus, another feature of the invention is considered to relate to the use of a diaphragm in which the length of a slit is ≧½ of the circumference of a needle (or cannula, etc.) inserted therein.

FIGS. 8–10 show embodiments of the present invention wherein the inventive diaphragm 30 has undergone a lesser degree of prechannelling than was required for the blunt cannula penetration taught by the prior art. FIG. 8a is a cross-sectional view of an inventive diaphragm 30 which shows a slit 31 which is biased in the closed position by forces as may be generated by the receptacle. The slit 31 extends from the top surface 32 through about a third or less, for example, of the thickness of the diaphragm, significantly less than the slits of the prior art. FIGS. 8b–8d show how a slit 31 may arise from the bottom 33 of the diaphragm, halfway for example, and thus leave an intact, easily cleanable top surface; or from an indented region 34 at the top of the diaphragm (FIG. 8c), through two-thirds of the septum, for example; or through about one-third of the thickness, between the top and bottom surfaces (FIG. 8d). According to the present series of inventions, said partial preslits 31 could be deepened by use of a convertor (Disclosure #II), widened by release of compressive forces (Disclosure #III) or use of a relatively pointed safety needle as described in the present disclosure. The height of the septum can be, for example, on the order of 0.125 inches (0.318 cm).

Figure 9A:
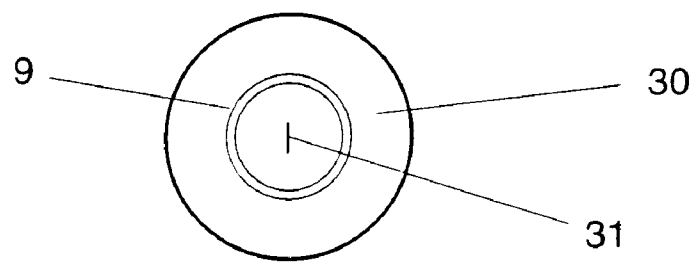
FIGS. 9a–9d are top views as they appear in embodiments of the present invention in which the preslits are incomplete and/or smaller (e.g., shorter, thinner, and/or less deep) than those required for the blunt cannula insertion of the prior art. Thus the diaphragm is weakened only slightly (in contrast to the more pronounced preslitting of prior art blunt cannula diaphragms). Likewise, in each of the configurations, the slit may lie totally beneath the diaphragm surface. According to the present invention, such preslits would use a relatively pointed safety needle since they would not be penetrable by a blunt cannula (unless the diaphragm was first modified as by penetration with a convertor —Disclosure #II).
Figure 9B:
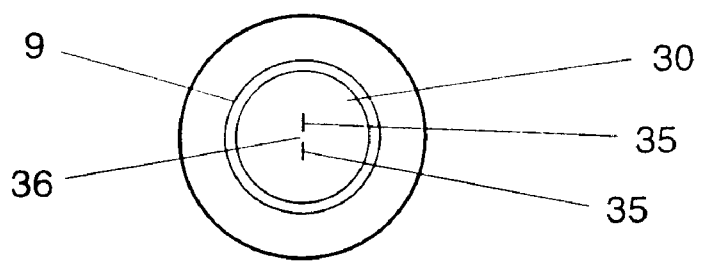
Figure 9C:
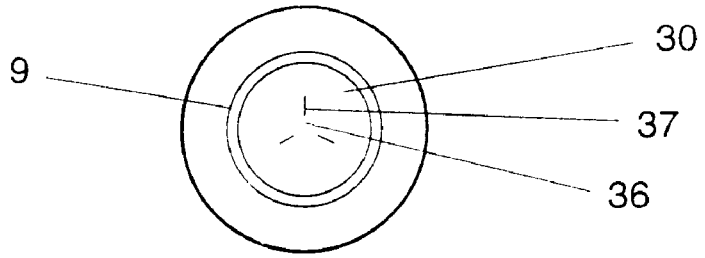
Figure 9D:
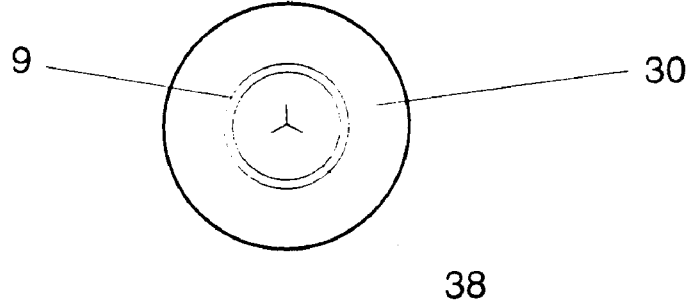

FIGS. 9a–9d are top views which illustrate embodiments of the present invention in which the channel(s) is (are) shorter than that of the prior art and can be lengthened and/or widened by insertion of a needle. In each of the illustrated embodiments, the site of penetration is surrounded by a raised rim or flat visual identifier such as a colored circle 9. FIG. 9a shows an embodiment of the inventive diaphragm 30 with a small slit 31. FIG. 9b shows a diaphragm 30 in which a divided slit 35 has a gap 36. FIG. 9c shows a gap 36 which needs to be pierced in order to extend and unite the arms of an array 37 of partial slits. FIG. 9d illustrates an array 38 of short slits which may be enlarged by a needle. For purposes of clarity, each of the embodiments shows the slit(s) extending to the top surface; however, the slit(s) may remain below the surface (as shown in FIG. 8) and thus leave the upper surface totally intact.

Figure 10A:
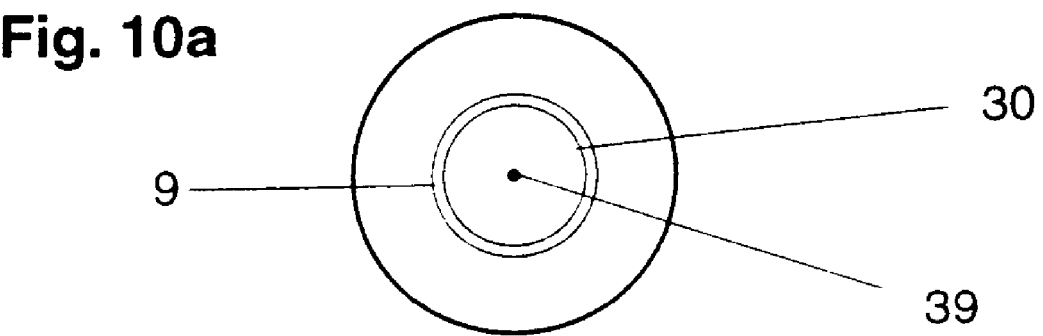
FIGS. 10a and 10b are top views as they appear in embodiments of the present invention in which the diaphragm has been constructed such that the partial prechannelling entails creation of a partial hole rather than a preslit at the time of manufacture. As for the slits in FIG. 9, said hole may lie totally beneath the surface (as suggested by the shading in FIG. 10b).
Figure 10B:
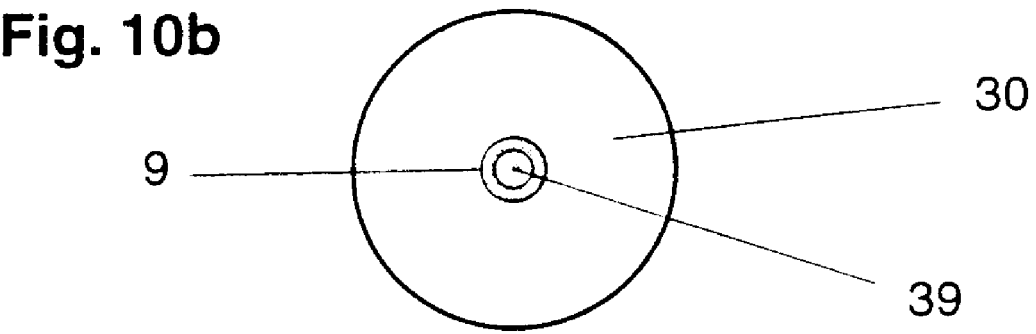

FIGS. 10a–10b illustrate a hole 39, as opposed to a slit, which may be sufficient when an inventive needle is inserted through a diaphragm 30. The hole may extend from the surface through the entire thickness of the diaphragm or it may extend only partway through or even lie below the surface. In the illustrated embodiment, the rim 9 encircles the recommended site of penetration. The diameter of the rim 9 can be reduced (as in FIG. 10b) to improve the accuracy of needle insertion. A marking or depression similarly may be used to identify the optimal site of insertion.

Figure 11A:
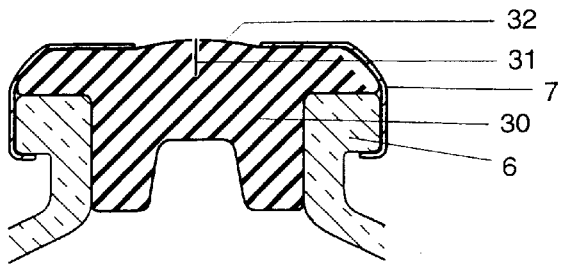
FIGS. 11a–11e show ways of maintaining diaphragm integrity despite the presence of a prechannelled region.
Figure 11B:
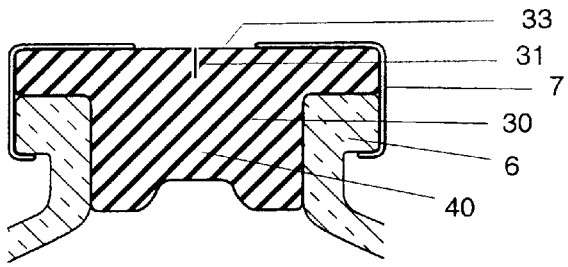
Figure 11C:
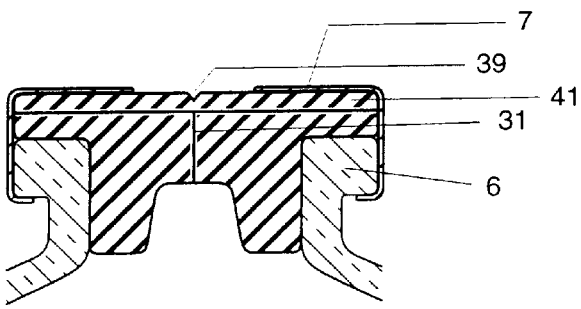
Figure 11D:
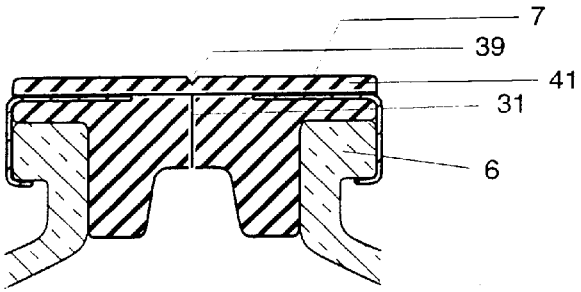
Figure 11E:
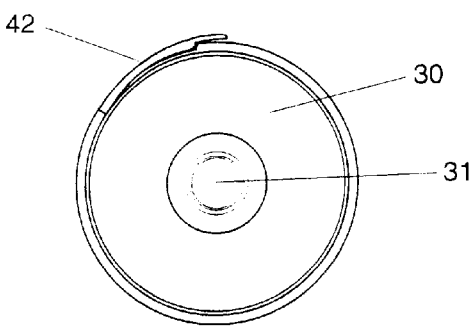

FIGS. 11a–11e illustrate arrangements for maintaining the integrity of a prechannelled diaphragm while still allowing penetration by a tapered needle or convertor. FIG. 11a shows that this may be accomplished by increasing axially directed compressive forces as may be achieved by inwardly curving the retaining (compressive) rim 7; this typically causes the top surface 32 to bulge outward. Other ways of increasing diaphragm integrity include: increasing the thickness of the region 40 of the diaphragm 30 that is below the prechannelled site 31 (FIG. 11b); providing an overlying membrane 41 which may lie above (FIG. 11c) or below (FIG. 11d) the rim 7; or compressing the diaphragm and its housing with a tight band 42 (FIG. 11e).

Figure 12:
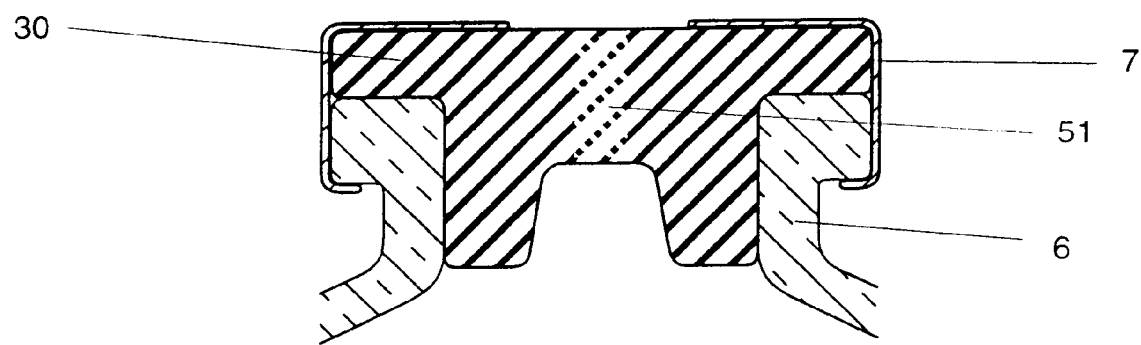
FIG. 12 is a cross-section of a diaphragm which has undergone ultrasonic weakening as described in the prior art.
Figure 13A:
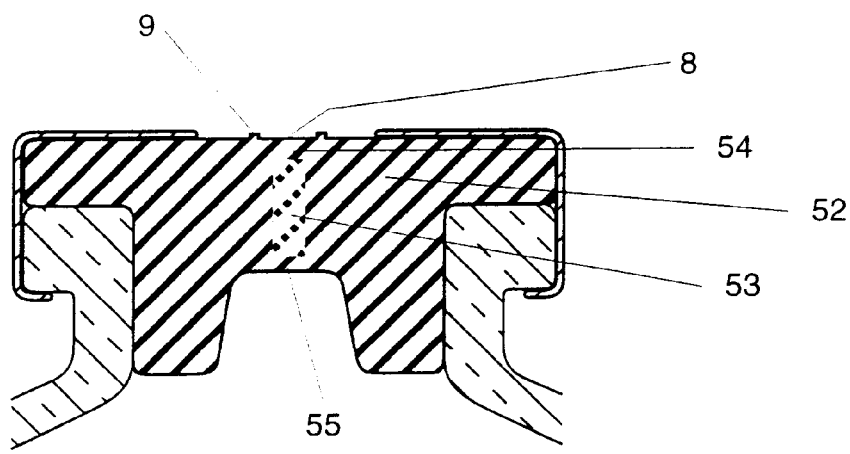
FIGS. 13a and 13b show embodiments of the present invention wherein the diaphragm has undergone ultrasonic weakening to a lesser degree than was required for blunt cannula penetration as taught by the prior art.
Figure 13B:
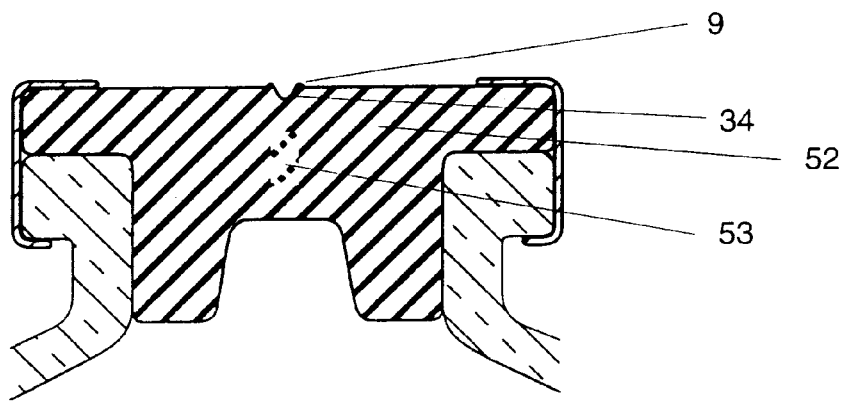

As illustrated in FIG. 12, prior art diaphragms designed for use with blunt cannulae may have a weakened area 51. One way in which this may be accomplished is by ultrasonic heating. FIGS. 13a and 13b show embodiments of the present invention wherein the inventive diaphragm 52 has a region 53 which has undergone ultrasonic weakening to a lesser degree than was required for blunt cannula penetration as taught by the prior art. The inventive series would allow this to be accomplished to a lesser degree by such methods as decreasing the joules generated per second or decreasing the duration for which the ultrasonic energy is applied, until the region is just weak enough to be penetrated by a corresponding needle. The integrity of the outer upper 54 and lower 55 portions may be better maintained by accelerating the removal of heat from these areas by increasing heat removal from the anvil and the horn as may be accomplished by increasing heat conductivity of the anvil and horn or cooling them with an external heat sink such as a water bath. The weakened area may be beneath a standard target site 8 FIG. 13a or a depressed site 34 FIG. 13b on the surface, each of which may be surrounded by a rim 9. An indentation not only identifies the site for insertion but it also forms a partially prechannelled region.

Each of the needles of the present invention is designed to meet the following criteria: a) puncture but not tear the matched diaphragm(s); b) have a lesser likelihood of transmitting inoculum by inadvertent skin puncture as a consequence of having less likelihood of puncturing the skin than a standard hypodermic needle and/or less likelihood of exposing the victim of such a puncture to the inoculum within the hollow bore of the needle; c) allow for the use of a diaphragm with greater sealing and/or resealing properties than the preslit or preweakened diaphragm of currently described needleless systems.

The long axis of each of the inventive hypodermic needles contains a hollow tubular channel (or through-bore) extending from the proximal hub end (which is structured for standard fluidic communication with other devices such as a syringe or infusion tubing) to one or more orifices located at the distal end. The orifice may be located at the end of taper. This so-called open-bevel design of the inventive series is tapered such that it is less sharp than a standard "dangerous and penetrating" needle.

Figures 14A, 14B:
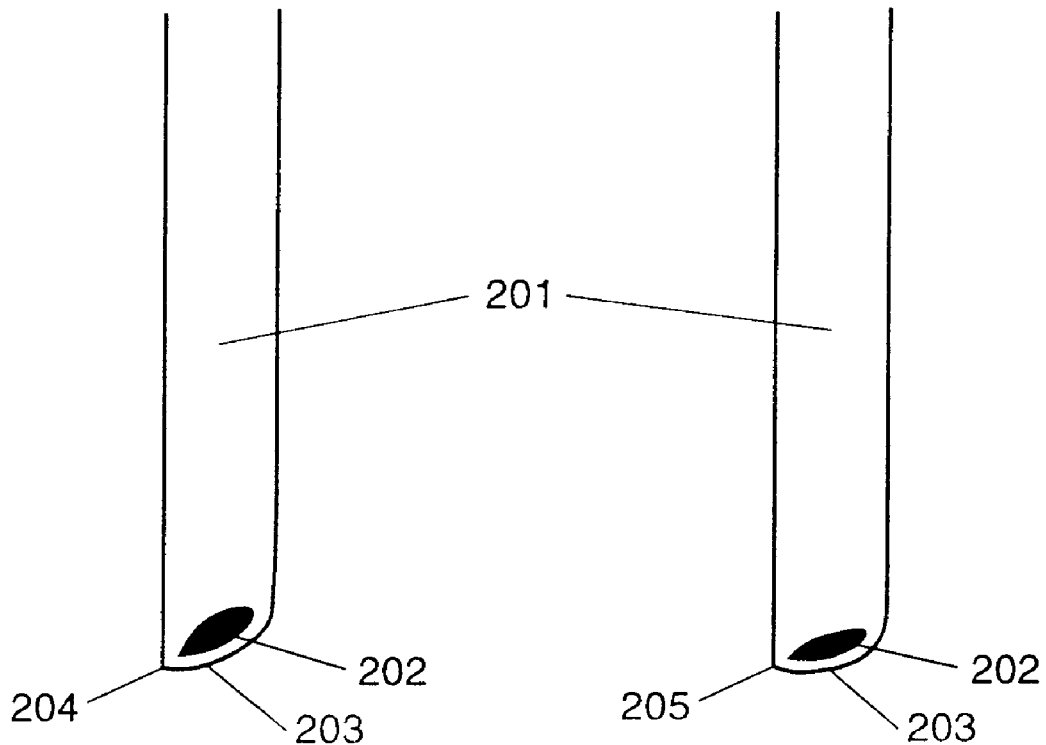
FIGS. 14a and 14b are examples of the approximate range of tapers and tips that is characteristic of the open-tipped embodiments of the inventive series: a) open tapered tip of approximately 30° to the plane perpendicular to the longitudinal axis of the needle (i.e., 60° to the axis of the needle; b) open tapered tip of approximately 15–20°.

FIGS. 14a and 14b show open-beveled tapered needles with a shaft 201, a tubular channel which ends in an opening 202 at the tip 203. The tip 203 may be any of several different angles to the plane which is perpendicular to the longitudinal axis of the needle, including the approximately 35° angle 204 (FIG. 14a) and the approximately 20° angle 205 (FIG. 14b).

In most of the embodiments, the orifice(s) is near, but not at, the actual tip. We believe that healhcare worker safety may be achieved more efficiently with the closed-tip design. The recessed orifices may be located at various distances from the needle tip. The hub may be marked to delineate orifice orientation. The channel may be midline or offset. The shaft may be thick-walled or thin-walled. The taper may be symmetrical or biased.

Figures 15A, 15B:
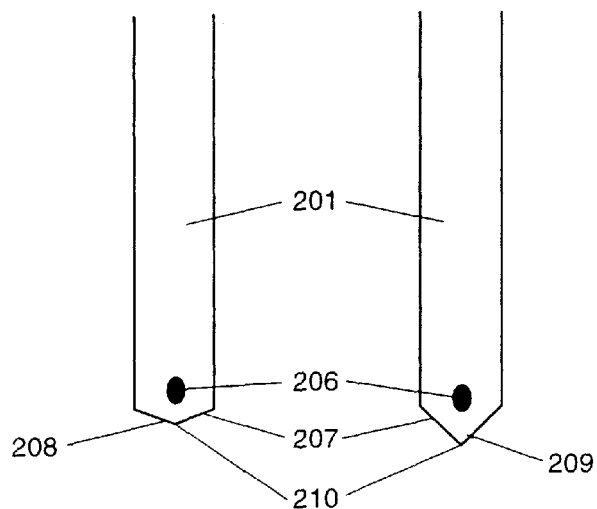
FIGS. 15a–15d are examples of the approximate range of tapers and tips that are characteristic of the closed-tipped embodiments of the inventive series: a) closed tapered tip of approximately 45°; b) closed tapered tip of approximately 20°.
Figures 15C, 15D:
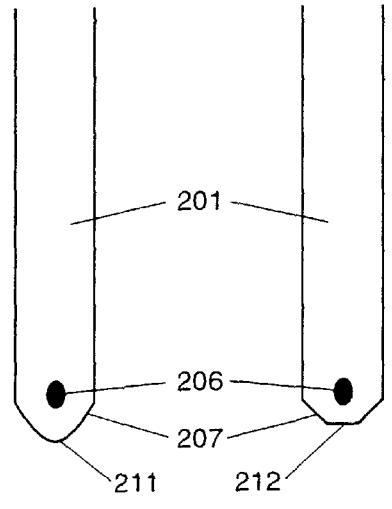

As illustrated in FIGS. 15a–15d, embodiments of the closed tip designs with recessed orifices 206 can have tips with tapers 207 ranging from approximately 15° (208 in FIG. 15a) to approximately 45° (209 in FIG. 15b). They may end in a pointed 210, rounded 211, or flat 212 distal end.

Each of the tapered inventive needles can penetrate more readily than a blunt cannula (FIG. 16), whose end 213 is essentially without a taper.

Several examples of orifice and channel designs are shown in FIGS. 17a–17p. The recessed orifices 206 of the present invention may be round, oval, angular or slitted. They may be chamfered to minimize tearing of tissues or penetrable diaphragms, and they may be fenestrated (covered with a screen or the like) to limit exposure of contaminants. They may be located anywhere on the taper 207 and/or on the shaft 201, and may arise from the end of the tubular channel 214 or emerge along the course of the channel. Their diameter may be greater than, less than, or equal to that of the main axial channel. In particular embodiments, orifices are located on the same side of the needle such that they will all drain if placed with that side down. Alternatively, in other embodiments, the orifices are spaced 180° from each other around the needle or have another suitable angular spacing to promote drainage regardless of the resting position of the needle. The presence of more than one orifice facilitates injection and aspiration. Particular attention is drawn to the oblique and/or curved course imparted to the passage between the main tubular channel(s) and each orifice 206 in many of the embodiments. This promotes drainage, thereby lessening the likelihood that a used needle would retain an inoculum.

Other aspects of the disclosed needles in FIGS. 17a–17p are shown in FIGS. 3a–3p and the corresponding text in U.S. Pat. No. 5,478,328, incorporated by reference.

FIGS. 18a–18f show embodiments of needles with retractable sheaths which are shown in FIGS. 11a–11c and 12a–12c and described at col. 12, lines 41 —col. 13, line 67 in U.S. Pat. No. 5,478,328, incorporated by reference, and are considered to be aspects of the present invention.

FIGS. 19a–19h show embodiments of needles with needle caps which are shown in FIGS. 13a–13d, 14a–14b and 15a–15b and described at col. 14, lines 1–col. 15, line 63 in U.S. Pat. 5,478,328, incorporated by reference, and are considered to be aspects of the present invention.

FIGS. 20a and 20b show examples of an inventive needle piercing an inventive (matched) diaphragm. FIG. 20a shows the process of inserting an inventive needle 214 with a recessed orifice 206 into an inventive diaphragm 30 with a channel 31. FIG. 20b shows a comparable process in an inventive diaphragm 52 with a partially weakened region 53.

TESTING OF NEEDLES, DIAPHRAGMS AND THEIR COMBINATIONS

Our goal is to use an inherently safe needle in combination with a diaphragm so long as the needle/diaphragm combination allows an effective degree of diaphragm integrity, efficient penetration, secure engagement, and resealability. Data to be collected include the following.

A. Diaphragm Effectiveness

1) Bacterial counts of fluids stored under seemingly sterile conditions in containers covered by the diaphragms under study before, during and after convertor and/or needle insertion. This can be determined for the anticipated duration of clinical use. For example, an intravenous line with injection ports typically is replaced every 48 hours; a single-use drug bottle should be discarded within minutes to hours, while a multi-use vial contains a preservative and should be discarded within 30 days after first use.

2) Integrity of the diaphragm in comparative studies. FIG. 21 shows a setup for comparing the ability of two or more diaphragms to resist leaking under identical conditions while fluid is delivered via tubing 301 or a syringe through a sealed orifice 302 over the range of temperatures, rates, pressures, and infusate consistencies that may be encountered during actual use. In the example, there are two diaphragm testing sites 303; an inventive diaphragm 30 with channel 31 is being compared to standard diaphragm 1. Additionally, the diaphragm can be compared during and after needle insertion(s). The inventive series of diaphragms will have integrity scores that exceed those of the needleless systems of the prior art since we are not limited to diaphragms which are penetrable by blunt cannulae from the time of manufacture (as described in the prior art). Likewise, the inventive systems will provide more secure engagement than blunt cannula needleless systems without supplemental means of securement. Whereas the prior art has not taught the use of needleless systems for covering openings wider than those covered by the diaphragms atop intravenous injection ports, an aforementioned advantage of the present invention is to enable use of a wider range of diaphragm sizes as may be required to cover openings atop wide-mouthed bottles. Their integrity can be tested by modifying the size of the openings 303 in the set-up illustrated in FIG. 21.

B. Needle Safety

1) Forces required for penetration of skin vs. diaphragm. A major advantage of the design and testing processes of the present investigation is to increase healthcare worker safety by designing needle/diaphragm combinations which, upon testing and subsequent clinical use, demonstrate a high diaphragm/skin penetrability ratio. The goal is to design systems where the force required to pierce the diaphragm (typically in the range of 2 to 5 lbs but desirably less preferable at most 50% in certain embodiments) should be decidedly less than that required to pierce the skin.

2) Arrangements to test the relative penetrabilities.

One such arrangement is shown in FIGS. 22a and 22b. A needle 214 is attached to a scale 310 such that the tip of the needle is pointed outward so as to measure the force required to pierce (or penetrate to a specific depth) skin as of the thumb 311 (FIG. 22a) or a diaphragm 312; the diaphragm may be supported independently or attached to the thumb (as shown in FIG. 22b).

A more elaborate testing system is illustrated in FIG. 23. A user's hand 313 is placed palm-side up under a strap (not shown) which limits the movement of all fingers except the thumb 311. The thumb 311 is then secured by a restraining device, such as a ring 314, which is attached to a pressure transducer 315 which measures the force of subsequent thumb movement. The needle 214 being tested is secured perpendicular to the thumb 311, with the needle point 210 touching or almost touching the palmar surface of the thumb 311 (FIG. 23a) or a diaphragm 312 attached to the thumb 311 (in FIG. 23b). (Alternatively, the needle can be attached to the thumb so as to puncture items placed in front of the thumb—not shown.) The thumb 311 may be advanced voluntarily. However, it is more reliable to induce a standardized forward thumb movement with a nerve stimulator whose stimulating electrodes 317 are placed over the ulnar nerve. The stimulating current causes thumb adduction by inducing contraction of the adductor pollicis muscle. The degree of contraction depends on the number of contracting fibers, which in turn is dependent on the stimulating current. The stimulating current can be increased in 1–2 milliampere increments, while the resultant force of contraction is recorded.

The standard stimulus used to elicit nerve firing in the assessment of neuromuscular function in the clinical setting (0.2 milliseconds in duration repeated at a rate of 0.1 Hz=once every 10 seconds) was used for our initial trial. It reliably induces movement consistent with that which is associated with accidental self-puncture. Stimuli of different duration and/or repetitive stimuli may be utilized. Preload may be added, as indicated, to alter the amount of thumb movement. Even greater reliability may be achieved in anesthetized subjects (who will not resist thumb advancement).

During testing with the setup illustrated in FIG. 23, we found that a standard open-bevel needle consistently punctured the skin such that blood appeared (and pain was felt) at 9–10 mm Hg pressure. (Lesser forces, due to lower currents, did not cause skin puncture.) In contrast, a sharp closed tip needle required a pressure of >15 mmHg to puncture the skin (and this was to a depth which did advance the orifice into the skin).

Needles and diaphragms designed in accordance with the present invention or for the same or other purposes according to other inventions can be tested and rated according to the aforementioned systems or in a comparable manner which would occur to those experienced in the art upon reading this disclosure. Such ratings may include, but are not necessarily be limited to, absolute force requirements for causing puncture of skin or diaphragm, as well as relative force requirements for piercing skin vs. diaphragm. The forces required for penetration to a depth that allows a needle's orifices to be advanced through the skin (and thus deliver an infectious inoculum) may be determined in a variety of ways, including recording the aforementioned penetrability studies on film.

Statistical data will include mean, median, standard deviation, standard error, as well as the confidence intervals, and coefficients of repeatability and variation. Embodiments of the inventive series will be compared to the Strong Diaphragm/Dangerous Needle and Weak Diaphragm/Safe Cannula combinations of the prior art. Ideally, the force required to puncture the skin should be many times greater than that required to penetrate a matched diaphragm. Needles also may be rated according to their incidence of skin puncture in clinical settings. Parametric data will be analyzed by paired t-testing and analysis of variance with appropriate modifications for multiple comparisons. Nonparametric data may be assessed using ranking techniques. Incidence (e.g. of skin penetration among different needles in different contexts) may be compared using Chi-squared analysis.

2. Force required for penetration to a depth such that the orifice(s) is (are) beneath the skin (and thus able to deliver an infectious inoculum).

The relative simplicity of the aforementioned means of testing enables rapid testing of a wide range of needles, diaphragms, and convertors. If deemed indicated, one can utilize the teaching of the prior art to guide initial testing. For example, for a needle with a diameter of 0.10 inch (0.254 cm), we will begin testing with a slit of the diameter recommended for absolutely blunt cannula in the prior art. The greater sharpness of the inventive needles will allow progressive decrease of the size of the slit to attain increased diaphragm integrity while seeking to ensure healthcare worker safety.

Thus, this disclosure teaches a combined testing procedure which addresses both testing of diaphragm integrity and penetrability as well as relative needle safety using combined indices, in connection with the design and testing of needle/diaphragm configurations.

What is claimed is:

1. A strong diaphragm/safe needle unit comprising:

a needle with a closed, solid tip and a longitudinal through-bore for fluidic communication from a proximal hub to at least one distal orifice, the at least one distal orifice being in communication with the bore of the needle and recessed from the solid tip;

wherein the solid tip is tapered at an angle of approximately between 45° and 75° to a longitudinal axis of the needle; and an elastically deformable diaphragm which is penetrable by the needle with a clinically acceptable force and which provides effective, leak-free closure after penetration.

2. The unit of claim 1, wherein the needle has a curved outlet passage for allowing an inoculum to exit from the needle.

3. The unit of claim 1, wherein the breaking strength of the diaphragm is substantially less than that of skin.

4. The unit of claim 1, wherein the breaking strength of the diaphragm is substantially less than that of skin.

5. The unit of claim 1, wherein the needle is covered by a sheath which in a resting state covers the at least one orifice and upon advancement of the needle through a diaphragm retracts to expose said orifice.

6. The unit of claim 1, wherein the diaphragm is substantially leakfree prior to initial use.

7. The unit of claim 1, wherein the diaphragm is not substantially damaged after engagement of the unit with the diaphragm.

8. The unit of claim 1, wherein the needle and diaphragm are mutually engageable upon said penetration.

9. The unit of claim 1, wherein the diaphragm has effective sealing after a single insertion and removal with the needle.

10. The unit of claim 1, wherein the diaphragm has effective sealing after multiple insertions and removals with the needle.

11. The unit of claim 1, wherein the diaphragm has effective sealing after a single insertion and removal with a sharp needle.

12. The unit of claim 1, wherein the diaphragm has effective sealing after multiple insertions and removals with a sharp needle.

13. The unit of claim 1, wherein the diaphragm has a slit or array of slits to facilitate penetration, wherein said slit or array extends partially through the thickness of the diaphragm.

14. The unit of claim 13, wherein the slit or array is extendable completely through the diaphragm by insertion of the needle.

15. The unit of claim 1, wherein the diaphragm has a hole to facilitate penetration, wherein said hole extends wholly through the thickness of the diaphragm.

16. The unit of claim 1, wherein the diaphragm has a weakened region to facilitate penetration.

17. The unit of claim 1, wherein the diaphragm is adaptable to cover bottles, tubes, bags, heparin locks and injection ports.

18. The unit of claim 1, wherein the diaphragm is penetrable by the needle.

19. The unit of claim 1, further comprising an injection site identifier carried by a housing of said diaphragm having indicia for identifying an injection site which is penetrable by the needle.

20. The unit of claim 19, wherein an intact surface of the diaphragm prior to penetration is wipeable without contamination.

21. The unit of claim 1, wherein the diaphragm has a slit or array of slits to facilitate penetration, wherein said slit or array of slits extends completely through the thickness of the diaphragm.

22. The unit of claim 1, wherein the diaphragm has a hole to facilitate penetration, wherein said hole extends partially through the thickness of the diaphragm.

23. The unit of claim 1, wherein said solid tip has a pointed end.

24. The unit of claim 1, wherein said solid tip has a rounded end.

25. The unit of claim 1, wherein said solid tip has a flat end.

26. A method of using a needle and a diaphragm,
wherein the needle has a solid tip and at least one longitudinal bore which terminates in one or more orifices which are in communication with the bore of the needle and recessed from the solid needle tip, and the diaphragm forms a seal on top of a container, and
wherein the solid tip is tapered at an angle of approximately between 45° and 75° to a longitudinal axis of the needle;
the method comprising the steps of:
puncturing the diaphragm with the solid tip of the needle; and
moving the solid tip of the needle through the diaphragm and advancing the one or more orifices into the container.

27. The method of claim 26, wherein said solid tip has a pointed end.

28. The method of claim 26, wherein said solid tip has a rounded end.

29. The method of claim 26, wherein said solid tip has a flat end.

* * * * *